(12) United States Patent
Alexandrov et al.

(10) Patent No.: US 7,361,749 B2
(45) Date of Patent: Apr. 22, 2008

(54) SEQUENCE-DETERMINED DNA ENCODING METHYLTRANSFERASES

(75) Inventors: Nickolai Alexandrov, Thousand Oaks, CA (US); Vyacheslav Brover, Simi Valley, CA (US); Kenneth Feldmann, Newbury Park, CA (US)

(73) Assignee: Ceres, Inc., Thousand Oaks, CA (US)

( * ) Notice: Subject to any disclaimer, the term of this patent is extended or adjusted under 35 U.S.C. 154(b) by 0 days.

(21) Appl. No.: 11/153,185

(22) Filed: Jun. 15, 2005

(65) Prior Publication Data

US 2006/0084796 A1 Apr. 20, 2006

Related U.S. Application Data

(63) Continuation-in-part of application No. 11/006,231, filed on Dec. 6, 2004, which is a continuation of application No. 10/645,822, filed on Aug. 22, 2003, which is a continuation-in-part of application No. 10/431,436, filed on May 8, 2003, now abandoned, which is a continuation-in-part of application No. 10/360,648, filed on Feb. 10, 2003, now abandoned, which is a continuation of application No. 10/277,279, filed on Aug. 26, 2002, now abandoned, which is a continuation of application No. 10/156,076, filed on May 29, 2002, now abandoned, which is a continuation of application No. 09/940,245, filed on Aug. 24, 2001, now abandoned, which is a continuation of application No. 09/940,256, filed on Aug. 24, 2001, now abandoned, which is a continuation-in-part of application No. 09/594,597, filed on Jun. 16, 2000, now abandoned, which is a continuation-in-part of application No. 09/513,996, filed on Feb. 25, 2000, now abandoned.

(60) Provisional application No. 60/139,463, filed on Jun. 18, 1999.

(51) Int. Cl.
*C12N 15/29* (2006.01)

(52) U.S. Cl. ............................................. 536/23.6

(58) Field of Classification Search .................. None
See application file for complete search history.

(56) References Cited

U.S. PATENT DOCUMENTS

| | | |
|---|---|---|
| 4,801,340 A | 1/1989 | Inoue et al. |
| 5,034,323 A | 7/1991 | Jorgensen et al. |
| 5,204,253 A | 4/1993 | Sanford et al. |
| 5,231,020 A | 7/1993 | Jorgensen et al. |
| 5,283,184 A | 2/1994 | Jorgensen et al. |
| 5,410,270 A | 4/1995 | Rybicki et al. |
| 5,445,934 A | 8/1995 | Fodor et al. |
| 5,538,880 A | 7/1996 | Lundquist et al. |
| 5,591,616 A | 1/1997 | Hiei et al. |
| 5,766,847 A | 6/1998 | Jackle et al. |
| 6,329,571 B1 | 12/2001 | Hiei |
| 2006/0143729 A1 | 6/2006 | Alexandrov et al. |

FOREIGN PATENT DOCUMENTS

| | | |
|---|---|---|
| DE | 10212703 | 3/2002 |
| EP | 1 033 405 | 9/2000 |
| EP | 6 255 72 | 4/2001 |
| WO | 95/35505 | 12/1995 |
| WO | 96/34981 | 11/1996 |
| WO | 98/07842 | 2/1998 |
| WO | 01/035725 | 5/2001 |
| WO | 03/013227 | 2/2003 |
| WO | 03/034812 | 5/2003 |
| WO | 05/054453 | 6/2005 |

OTHER PUBLICATIONS

GenBank Accession No. CAB87794, dated Nov. 14, 2006.
GenBank Accession No. BAB62076, dated Feb. 14, 2004.
GenBank Accession No. NP 191900, dated Apr. 20, 2007.
GenBank Accession No. AAM63077, dated Jan. 27, 2006.
GenBank Accession No. ABF85788, dated Jun. 7, 2006.
Alonso-Blanco et al., Methods in Molecular Biology, vol. 82, "Arabidopsis Protocols", pp. 137-146, J.M. Martinez-Zapter and J. Salinas, eds., c. 1998 by Humana Press, Totowa, NJ.
Armaleo et al., "Biolistic nuclear transformation of *Saccharomyces cerevisiae* and other fungi" *Current Genetics*, 17:97 (1990).
Ausubel et al. 1992 (Current Protocols in Molecular Biology, Greene Publishing, New York) pp. 8-1-8-25.
Azpiroz-Leehan et al., "T-DNA insertion mutagenesis in *Arabidopsis*: going back and forth" Trends *in Genetics*, 13:152 (1997).
Baerson et al., "Development regulation of an acyl carrier protein gene promoter in vegetative and reproductive tissues" *Plant Mol. Biol.*, 22(2):255-267 (1993).
Bateman et al., "Pfam 3.1: 1313 multiple alignments and profile HMMs match the majority of proteins" *Nucl. Acids Res.*, 27:260-262 (1999).
Bechtold et al., "*In planta Agrobacterium* mediated gene transfer by infiltration of adult *Arabidopsis thaliana* plants" *C.R. Acad. Sci. Paris*, 316:1194-1199 (1993).
Blattner et al., "The complete genome sequence of *Escherichia coli* K-12" *Science*, 277:1453 (1997).
Bonner et al., "Reduction in the rate of DNA reassociation by sequence divergence" *J. Mol. Biol.*, 81:123 (1973).
Bustos et al., "Regulation of β-Glucuronidase expression in transgenic tobacco plants by an A/T-rich, *cis*-Acting sequence found upstream of a French bean β-Phaseolin gene" *The Plant Cell*, 1:839-854 (1989).

(Continued)

*Primary Examiner*—James Martinell
(74) *Attorney, Agent, or Firm*—Fish & Richardson P.C.

(57) ABSTRACT

The present invention provides DNA molecules that constitute portions of the genome of a plant. The DNA molecules are useful for expressing a gene product, either as a promoter or as a structural gene or as an UTR or as an 3' termination sequence and are also useful in controlling expression of the target gene or as tools for genetic mapping or identification of a particular individual plant or for clustering of a group of plants with a common trait.

1 Claim, No Drawings

OTHER PUBLICATIONS

Carels et al., "Compositional properties of homologous coding sequences from plants" *J. Mol. Evol.*, 46:45 (1998).
Cerdan et al., "A 146 bp fragment of the tobacco Lhcbl*2 promoter confers very-low-fluence, low-fluence and high-irradiance responses of phytochrom to a minimal CaMV 35S promoter" *Plant Mol. Biol.*, 33:245-255 (1997).
Chang et al., "The Exo-gap method employing the phage fl endonuclease generates a nested set of unidirectional deletions" *Gene*, 127:95 (1993).
Chen et al., "Functional analysis of regulatory elements in a plant embryo-specific gene" *Proc. Natl. Acad. Sci. USA*, 83:8560-8564 (1986).
Chen et al. "Expression profile matrix of arabidopsis transcription factor genes suggest their putative functions in response to environmental stresses" *The Plant Cell*, 14:559-574 (2002).
Cho et al. "Expression of gamma-tocopherol methyltransferase transgene improves tocopherol composition in lettuce" *Molecules and Cells*, 19(1):16-22 (2005).
Christou, "Strategies for variety-independent genetic transformation of important cereals, legumes and woody species utilizing particle bombardment" *Euphytica*, 85(1-3):13-27, (1995).
Collakova et al. "The role of homogentisate phytyltransferase and other tocopherol pathway enzymes in the regulation of tocopherol synthesis during abiotic stress" *Plant Physiology*, 133(2):930-940 (2003).
Conkling et al. "Isolation of transcriptionally regulated root-specific genes from tobacco", *Plant Physiol.*, 1990, 93:1203-1211.
Cox et al., "Plant Molecular Biology: A Practical Approach", pp. 1-35, Shaw ed., c. 1988 by IRL, Oxford.
"Genome sequence of the nematode C. elegans: a platform for investigating biology" *Science* 282:2012 (1998) The C. elegans Sequencing Consortium.
Escudero et al., "T-DNA transfer in meristematic cells of maize provided with intracellular *Agrobacterium*" *Plant J.*, 10:355 (1996).
Evans et al., Protoplasts Isolation and Culture in "Handbook of Plant Cell Culture," pp. 124-176, *MacMillilan Publishing Company*, New York, 1983.
Fejes et al., "A 268 bp upstream sequence mediates the circadian clock-regulated transcription of the wheat Cab-1 gene in transgenic plants" *Plant Mol. Biol.*, 15:921-932 (1990).
Fennoy et al. "Synonymous codon usage in Zea mays L. nuclear genes is varied by levels of C and G-ending codons" *Nucleic Acids Research*, 21(23):5294 (1993).
Fromm et al. "Expression of genes transferred into monocot and dicot plant cells by electroporation" *Proc. Natl. Acad. Sci. USA*, 82:5824 (1985).
Fromm et al., "An octopinge synthase enhancer element directs tissue-specific expression and binds ASF-1, a factor from tobacco nuclear extracts" *The Plant Cell*, 1:977-984 (1989).
Fry et al., "A new approach to template purification for sequencing applications using paramagnetic particles" *Biotechniques*, 13: 124 (1992).
Biswas et al. "Trangenic Indica rice (*Oryza sativa* L.) plants obtained by direct gene transfer to protoplasts" *J. Biotechnol.*, 32:1 (1994).
Gleave, AP., "A versatile binary vector system with a T-DNA organizational structure conducive to efficient integration of cloned DnA into the plant genome"*Plant Mol. Biol.* 20:1203 (1992).
Gould et al., "Transformation of Zea mays L. Using *Agrobacterium tummefaciens* and the shoot apex" *Plant Physiology*, 95:426 (1991).
Graves and Goldman, "The transformation of Zea mays seedling with *Agrobacterium tumefaciens*" *Plant Mol. Biol.*, 45 (1986).
Guilfoyle, "Ligation-mediated PCR amplification of specific fragments from a class-II restriction endonuclease total digest" *Nucleic Acids Res.*, 25:9, 1854 (1997).
Hamilton, "A binary-BAC system for plant transformation with high-molecular-weight DNA" *Gene*, 200:107-116 (1997).
Haseloff et al. "Simple RNA enzymes with new and highly specific endoribonuclease activities" *Nature*, 334:585 (1988).
Herrera-Estrella et al., "Chimeric genes as dominant selectable markers in plant cell" *EMBO J.*, 2:987 (1983).

Hong et al., "Promter sequences from two different *Brassica napus* tapetal oleosin-like genes direct tapetal expression of β-glucuronidase in transgenic *Brassica* plants" *Plant Mol Biol.*, 1997 34(3):549-555.
Hosoyama et al. "Oryzacystatin exogenously introduced into protoplasts and regeneration of transgenic rice" *Biosci. Biotechnol. Biochem.* 58:1500 (1994).
Hwang and Goodman, "An *Arabidopsis thaliana* root-specific kinase homolog is induced by dehydration, ABA, and NaCl" *Plant J.* 8:37 (1995).
Ishida et al., "High efficiency transformation of maize (*Zea mays* L. mediated by *Agrobacterium tumefaciens*" *Nature Biotechnology*, 14:745 (1996).
Kanwischer et al. "Alterations in tocopherol cyclase activity in transgenic and mutant plants of Arabidopsis affect tocopherol content, tocopherol composition, and oxidative stress" *Plant Physiology*, 137:713-723 (2005).
Kato et al., "Construction of a human full-length cDNA bank" *Gene* 150:243-250 (1994).
Keller and Manak "DNA Probes", 2nd Ed. pp. 1-25, c. 1993 by Stockton Press, New York, NY.
Klee et al. "Agrobacterium-mediated plant transformation and its further applications to plant biology" *Ann. Rev. of Plant Phys.*, 38:467 (1987).
McCormac et al., "A flexible series of binary vectors for agrobacterium-mediated plant transformation" *Mol. Biotechnol.*, 8:199 (1997).
Motohasi et al. "Functional analysis of the 37 kDa inner envelope membrane polypeptide in choloroplast biogenesis using a Ds-tagged *Arabidopsis* pale-green mutant" *The Plant Journal*, 34(5):719-731 (2003).
Müller et al., "High meiotic stability of a foreign gene introduced into tobacco by *Agrobacterium*-mediated transformation" *Mol. Gen. Genet.*, 207:171 (1987).
Napoli et al., "Introduction of a chimeric chalcone synthase gene into petunia results in reversible co-suppression of homologous genes in trans." *The Plant Cell*, 2:279 (1990).
Needleman and Wunsch "A general method applicable to the search for similarities in the amino acid sequence of two proteins" *J. Mol. Biol.*, 48:443 (1970).
Oeller et al., "Reversible inhibition of tomato fruit senescence by antisense RNA" *Science*, 254:437-439 (1991).
Paszkowski et al. "Direct gene transfer to plants" *EMBO J.*, 3:2717 (1984).
Pearson and Lipman "Improved tools for biological sequence comparison" *Proc. Natl. Acad. Sci. USA*, 85: 2444 (1988).
Refseth et al., "Hybridization capture of microsatellites directly from genomic DNA" *Electrophoresis*, 18:1519 (1997).
Riggs et al., "Cotyledon nuclear proteins bind to DNA fragments harboring regulatory elements of phytohemagglutinin genes" *Plant Cell*, 1(6):609-621 (1989).
Rivera et al, "Genomic evidence for two functionally distinct gene classes" *Proc. Natl. Acad. Sci. USA*, 1998, 95:6239-6244.
Salomon et al., "Genetic identification of functions of TR-DNA transcripts in octopine crown galls" *EMBO J.*, 3:141 (1984).
Sambrook et al., 1989, "Molecular Cloning, A Laboratory Manual", second edition, *Cold Spring Harbor Press*, Plainview; NY, pp. 4.21-4.41.
Seki et al., "Hig-efficiency cloning of *Arabidopsis* full-length cDNA by biotinylated CAP trapper" Plant Journal 15(5): 707-720 (1998).
Sheehy et al., "Reduction of polygalacturonase activity in tomato fruit by antisense RNA" *Proc. Nat. Acad. Sci. USA*, 85:8805 (1988).
Shintani et al. "Elevating the vitamin E content of plants through metabolic engineering" *Science*, 282(5396):2098-2100 (1998).
Slocombe et al., "Temporal and tissue-specific regulation of a *Brassica napus* stearoyl-acyl carrier protein desaturase gene" *Plant Physiol.*, 1994, 104(4):167-176.
Smith and Waterman, "Comparison of Biosequences" *Advances in Applied Mathematics.*, 2:482 (1981).
Sonnhammer et al., "Pfam: A comprehensive database of protein domain families based on seed alignments" *Proteins*, 28:405-420 (1997).

Sonnhammer et al., "Pfam: multiple sequence alignments and HMM-profiles of protein domains" *Nucl. Acids Res.*, 26:320-322 (1998).

Tijessen, "Hybridization with Nucleic Acid Probes" in Laboratory Techniques in Biochemistry and Molecular Biology, P.C. vand der Vliet, ed., c. 1993 by *Elsevier*, Amsterdam, pp. 19-78.

Truernit et al., "The promoter of the Arabidopsis thaliana SUC2 sucrose-H$^+$ symporter gene directs expression of β-glucuronidase to the phloem: Evidence for phloem loading and unloading by SUC2" *Planta.* 196:564-570 (1995).

Urdea et al. "Chemical synthesis of a gene for human epidermal growth factor urogastrone and its expression in yeast" *Proc. Natl. Acad. Sci. USA* 80:7461 (1983).

van der Krol et al., "Flavonoid genes in petunia: Addition of a limited number of gene copies my lead to a suppression of gene expression" *The Plant Cell*, 2:291 (1990).

Venkateswarlu et al., "Evidence for T-DNA mediated gene targeting to tobacco chloroplasts" *Biotechnology*, 9:1103 (1991).

Vergunst et al., "Site-specific integration of *Agrobacterium* T-DNA in *Arabidopsis thaliana* mediated by Cre recombinase" *Nucleic Acids Res.*, 26:2729 (1998).

Weising et al., "Foreign genes in plants: transfer, structure, expression, and applications" *Ann. Rev. Genet.*, 22:421 (1988).

Williams et al., "Development of a PCR-based allele-specific assay from a RFLP probe linked to resistance to cereal cyst nematode in wheat" *Genome*, 39:7, 798 (1996).

Xu et al., "Characteerization of a rice gene family encoding root-specific protein" *Plant Molecular Biology.* 27:237 (1995).

Yamamoto et al., "Characterization of *cis*-Acting sequences regulating root-specific gene expression in tobacco" *Plant Cell*, 3:371 (1991).

Yamamoto et al., "The promoter of a pine photosynthetic gene allows expression of a β-glucuronidase reporter gene in transgenic rice plants in a light-independent but tissue-specific manner" *Plant Cell Physiol.*, 1994 35:773-778.

Zheng et al., "*SPK1* is an Essential S-Phase-Specific Gene of *Saccharomyces cerevisiae* that encodes a nuclear serine/threonine/tyrosine kinase" *Mol. Cell Biol.*, 1993, 13:5829-5842.

Office Action from U.S. Appl. No. 11/180,418, document dated May 17, 2007, 10 pages; Sep. 17, 2007 Response to Office Action dated May 17, 2007, 10 pages.

Office Action from U.S. Appl. No. 11/357,357, document dated May 17, 2007, 9 pages; Sep. 17, 2007 Response to Office Action dated May 17, 2007, 9 pages.

Office Action from U.S. Appl. No. 11/362,546, document dated Nov. 15, 2006, 6 pages; Feb. 14, 2007 Response to Office Action dated Nov. 15, 2006, 7 pages.

Final Office Action from U.S. Appl. No. 11/362,546, document dated May 2, 2007, 6 pages; Jul. 2, 2007 Response to Final Office Action dated May 2, 2007, 16 pages.

Office Action from U.S. Appl. No. 11/369,193, document dated Nov. 15, 2006, 7 pages; Feb. 14, 2007 Response to Office Action dated Nov. 15, 2006, 11 pages.

Office Action from U.S. Appl. No. 11/369,173, document dated Nov. 115, 2006, 15 pages; Feb. 14, 2007 Response to Office Action dated Nov. 15, 2006, 6 pages.

Office Action from U.S. Appl. No. 11/369,173, document dated May 3, 2007, 10 pages.

Klein et al. "High-velocity microprojectiles for delivering nucleic acids into living cells" *Nature*, 327: 70 (1987).

Kohler and Milstein "Continuous cultures of fused cells secreting antibody of predefined specificity" *Nature*, 256: 495 (1975).

Komari et al., "Vectors carrying two separate T-DNAs for co-transformation of higher plants mediated by *Agrobacterium tumefaciens* and segregation of transformants free from selection markers" *Plant J.*, 10:165 (1996).

Koltonow et al., "Different temporal and spatial gene expression patterns occur during anther development" *Plant Cell*, 2:1202 (1990).

Lam et al., "Site-specific mutations in alter in vitro factor binding and change promoter expression pattern in transgenic plants" *Proc. Natl. Acad. Sci. USA*, 86:7890-7894 (1989).

Lee et al., "A C-methyltransferase involved in both ubiquinone and menaquinone biosynthesis: isolation and identification of the *Escherichia coli* ubiE gene" *J. Bacteriol.* 179:1748-1754 (1997).

Luan et al., "A rice *cab* gene promoter contains separate *cis*-acting elements that regulate expression in dicot and monocot plants" *The Plant Cell*, 4:971-973 (1992) only.

Lubberstedt et al., "Promoters from genes for plastid proteins possess regions with different sensitivities toward red and blue light" *Plant Physiol.*, 104:997-1006 (1994).

Mariani et al., "A chimaeric ribonuclease-inhibitor gene restores fertility to male sterile plants" *Nature*, 357: 384-387 (1992).

Maruyama et al., "Oligo-capping: a simple method to replace the cap structure of eukaryotic mRNAs with oligoribonucleotides" *Gene* 138:171 (1994).

Matsuoka et al., "Tissue-specific light-regulated expression directed by the promoter of a C4 gene, maize pyruvate, orthophosphate dikinase, in a C3 plant, rice" *Proc. Natl. Acad. Sci. USA*, 90:9586-9590 (1993).

Matteucci et al. "Synthesis of Deoxyoligonucleotides on a polymer support" *J. Am. Chem. Soc.*, 103:3185 (1981).

May et al., "Generation of transgenic banana (*Musa acuminate*) plants via *Agrobacterium*-mediated transformation" *Bio/Technology*, 13:486 (1995).

Office Action from U.S. Appl. No. 11/370,240, dated Sep. 27, 2007, 8 pages.

Final Office Action from U.S. Appl. No. 11/357,357, dated Nov. 29, 2007, 9 pages.

Final Office Action from U.S. Appl. No. 11/180,418, dated Nov. 30, 2007, 10 pages.

Office Action from U.S. Appl. No. 11/370,253, dated Oct. 30, 2007, 20 pages.

Office Action from U.S. Appl. No. 11/371,356, dated Oct. 30, 2007, 20 pages.

Office Action from U.S. Appl. No. 11/371,624, dated Oct. 31, 2007, 21 pages.

Office Action from U.S. Appl. No. 11/396,357, dated Nov. 7, 2007, 7 pages.

Office Action from U.S. Appl. No. 11/371,623, dated Nov. 16, 2007, 10 pages.

Office Action from U.S. Appl. No. 11/369,168, dated Oct. 30, 2007, 20 pages.

Notice of Allowance from U.S. Appl. No. 11/367,760, dated Oct. 5, 2007, 6 pages.

Notice of Allowance from U.S. Appl. No. 11/372,369, dated Nov. 13, 2007, 7 pages.

Notice of Allowance from U.S. Appl. No. 11/396,378, dated Nov. 13, 2007, 7 pages.

SEQUENCE-DETERMINED DNA ENCODING METHYLTRANSFERASES

RELATED-APPLICATIONS

This application is a continuation-in-part of U.S. patent application Ser. No. 11/006,231 filed Dec. 6, 2004, which is a continuation of U.S. patent application Ser. No. 10/645,822 filed Aug. 22, 2003, which is a continuation-in-part of U.S. patent application Ser. No. 09/513,996 filed on Feb. 25, 2000, which claims the benefit of priority to U.S. Provisional Patent Application No. 60/139,463, filed Jun. 18, 1999; (b) this application also is a continuation-in-part of U.S. patent application Ser. No. 11/006,231 filed Dec. 6, 2004, which is a continuation of U.S. patent application Ser. No. 10/645,822 filed Aug. 22, 2003, which is a continuation-in-part of U.S. patent application Ser. No. 10/431,436 filed on May 8, 2003, which is a continuation of U.S. patent application Ser. No. 10/227,279 filed Aug. 26, 2002, which is a continuation of U.S. patent application Ser. No. 09/940,245 filed Aug. 24, 2001, which is a continuation-in-part of U.S. patent application Ser. No. 09/594,597 filed Jun. 16, 2000, which claims the benefit of priority to U.S. Provisional Patent Application No. 60/139,463, filed Jun. 18, 1999; and (c) this application also is a continuation-in-part of U.S. patent application Ser. No. 11/006,231 filed Dec. 6, 2004, which is a continuation of U.S. patent application Ser. No. 10/645,822 filed Aug. 22, 2003, which is a continuation-in-part of U.S. patent application Ser. No. 10/360,648 filed on Feb. 10, 2003, which is a continuation of U.S. patent application Ser. No. 10/156,076 filed May 29, 2002, which is a continuation of U.S. patent application Ser. No. 09/940,256 filed Aug. 24, 2001, which is a continuation-in-part of U.S. patent application Ser. No. 09/594,597 filed Jun. 16, 2000, which claims the benefit of priority to U.S. Provisional Patent Application No. 60/139,463, filed Jun. 18, 1999. The entire contents of these related applications are incorporated by reference in their entirety.

BACKGROUND

1. Technical Field

The present invention relates to isolated polynucleotides that encode all, or a portion of, a gene that is expressed and the corresponding polypeptide. The present invention also relates to isolated polynucleotides that encode regulatory regions of genes.

2. Background Information

Efforts to map and sequence the genome of a number of organisms are in progress; a few complete genome sequences, for example those of *E. coli* and *Saccharomyces cerevisiae* are known (Blattner et al., Science 277:1453 (1997); Goffeau et al., Science 274:546 (1996)). The complete genome of a multicellular organism C. elegans has also been sequenced (See, the *C. elegans* Sequencing Consortium, Science 282:2012 (1998)). To date, no complete genome of a plant has been sequenced, nor has a complete cDNA complement of any plant been sequenced.

SUMMARY

The present invention comprises polynucleotides, such as cDNA sequences and/or genomic fragments, hereinafter collectively referred to as "Sequence-Determined DNA Fragments" (SDFs), from *Arabidopsis thaliana* and polypeptides derived therefrom. In some instances, the SDFs span the entirety of a protein-coding segment. In some instances, the entirety of an mRNA is represented. Other objects of the invention are the control sequences such as, but not limited to, promoters that are also represented by SDFs of the invention.

Other objects of the invention are polynucleotides comprising intron sequences, polynucleotides comprising introns together with exons, intron/exon junction sequences, 5' untranslated sequences, and 3' untranslated sequences of the SDFs of the present invention.

The present invention also resides in probes useful for isolating and identifying nucleic acids that hybridize to an SDF of the invention. The probes are typically of a length of 12 to 2000 nucleotides long; more typically, 15 to 200 nucleotides long; even more typically, 18 to 100 nucleotides long.

Yet another object of the invention is a method of isolating and/or identifying nucleic acids using the following steps:

(a) contacting a probe of the instant invention with a polynucleotide sample under conditions that permit hybridization and formation of the polynucleotide duplex; and (b) detecting and/or isolating the duplex of step (a). The conditions for hybridization can be from low to moderate to high stringency conditions. The sample can include a unique sequence in a plant genome. Probes and methods of the invention are useful, for example, without limitation, for mapping of genetic traits and/or for positional cloning of a desired portion of genomic DNA. Probes and methods of the invention can also be used for detecting related genes in other plant species in genomic DNA (gDNA) and/or cDNA libraries. In some instances, especially when longer probes and low to moderate stringency hybridization conditions are used, the probe will hybridize to a plurality of cDNA and/or gDNA sequences of a plant. This approach is useful for isolating representatives of gene families which are identifiable by possession of a common functional domain in the gene product or which have common cis-acting regulatory sequences. This approach is also useful for identifying orthologous genes from other organisms, which can be more or less related to *Arabidopsis*.

The present invention also resides in constructs for modulating the expression of the genes comprised of all or a portion of an SDF. The constructs comprise all or a portion of the expressed SDF, or of a complementary sequence. Examples of constructs include ribozymes comprising RNA encoded by an SDF or by a sequence complementary thereto, antisense constructs, constructs comprising coding regions or parts thereof, constructs comprising promoters, introns, untranslated regions, etc. When inserted into a host cell the construct is preferably integrated or operatively linked to a heterologous polynucleotide. For instance, a coding region from an SDF might be operably linked to a promoter that is functional in a plant.

The present invention also resides in host cells, including bacterial or yeast cells or plant cells, and transgenic plants that harbor constructs such as described above. Another aspect of the invention relates to methods for modulating expression of specific genes in transgenic plants by expression of the structural gene component of the constructs, by regulation of expression of one or more endogenous genes in a transgenic plant or by suppression of expression the polynucleotides of the invention in a transgenic plant. Methods of modulation include without limitation (1) inserting into a host cell additional copies of a polynucleotide comprising a coding sequence; (2) modulating a endogenous promoter in a host cell; (3) inserting antisense or ribozyme constructs into a host cell and (4) inserting into a host cell a polynucleotide comprising a sequence encoding a mutant, fragment, or fusion of the native polypeptides of the instant invention.

BRIEF DESCRIPTION OF THE TABLES

The SDFs of the instant invention are listed in Table 2; annotations relevant to the sequences shown in Table 2 are presented in Table 1. Each sequence corresponds to a clone number. Each clone number corresponds to at least one sequence in Table 2. The nucleotide sequence in Table 2 is a "Maximum Length Sequence" (MLS) that is the sequence of an insert in a single clone.

Table 1 is a Reference Table which correlates each of the sequences and SEQ ID NOs in Table 2 with a corresponding Ceres clone number, Ceres sequence identifier, and other information about the individual sequence. Table 2 is a Sequence Table with the sequence of each nucleic acid and amino acid sequence.

In Table 1, each section begins with a line that identifies the corresponding internal Ceres clone by its ID number. Subsection (A) then provides information about the nucleotide sequence including the corresponding sequence in Table 2, and the internal Ceres sequence identifier ("Ceres seq_id"). Subsection (B) provides similar information about a polypeptide sequence, but additionally identifies the location of the start codon in the nucleotide sequence which codes for the polypeptide. Subsection (C) provides information (where present) regarding identified domains within the polypeptide and (where present) a name for the polypeptide. Finally, subsection (D) provides (where present) information concerning amino acids which are found to be related and have some sequence identity to the polypeptide sequences of Table 2. Those "related" sequences identified by a "gi" number are in the GenBank data base.

In Table 2, Xaa within an amino acid sequence denotes an ambiguous amino acid. An Xaa at the end of an amino acid sequence indicates a stop codon.

TABLE 1

Reference table.
Maximum Length Sequence corresponding to clone ID 19143

(A) Polynucleotide Sequence
    Pat. Appln. SEQ ID NO: 1 (SEQ ID NO: 1542 in U.S. patent application Ser. No. 60/139,463)
    Ceres seq_id 1027295
  (B) Polypeptide Sequence
    Pat. Appln. SEQ ID NO: 2 (SEQ ID NO: 1543 in U.S. patent application Ser. No. 60/139,463)
    Ceres seq_id 1027296
    Location of start within SEQ ID NO 1: at 83 nt.
  (C) Nomination and Annotation of Domains within Predicted Polypeptide(s)
    Alignment No. 18179
    ubiE/COQ5 methyltransferase family
    Location within SEQ ID NO 2: from 70 to 257 aa.
  (D) Related Amino Acid Sequences
    Alignment No. 18180
    gi No. 124429
    % Identity 74.1
    Alignment Length 347
    Location of Alignment in SEQ ID NO 2: from 1 to 338
    Alignment No. 18181
    gi No. 1419090
    % Identity 75.7
    Alignment Length 339
    Location of Alignment in SEQ ID NO 2: from 1 to 338
    Alignment No. 18182
    gi No. 728630
    % Identity 71

TABLE 1-continued

Reference table.
Maximum Length Sequence corresponding to clone ID 19143

Alignment Length 62
    Location of Alignment in SEQ ID NO 2: from 277 to 338
(B) Polypeptide Sequence
    Pat. Appln. SEQ ID NO: 3 (SEQ ID NO: 1544 in U.S. patent application Ser. No. 60/139,463)
    Ceres seq_id 1027297
    Location of start within SEQ ID NO 1: at 95 nt.
(C) Nomination and Annotation of Domains within Predicted Polypeptide(s)
    Alignment No. 18183
    ubiE/COQ5 methyltransferase family
    Location within SEQ ID NO 3: from 66 to 253 aa.
(D) Related Amino Acid Sequences
    Alignment No. 18184
    gi No. 124429
    % Identity 74.1
    Alignment Length 347
    Location of Alignment in SEQ ID NO 3: from 1 to 334
    Alignment No. 18185
    gi No. 1419090
    % Identity 75.7
    Alignment Length 339
    Location of Alignment in SEQ ID NO 3: from 1 to 334
    Alignment No. 18186
    gi No. 728630
    % Identity 71
    Alignment Length 62
    Location of Alignment in SEQ ID NO 3: from 273 to 334
(B) Polypeptide Sequence
    Pat. Appln. SEQ ID NO: 4 (SEQ ID NO: 1545 in U.S. patent application Ser. No. 60/139,463)
    Ceres seq_id 1027298
    Location of start within SEQ ID NO 1: at 371 nt.
(C) Nomination and Annotation of Domains within Predicted Polypeptide(s)
    Alignment No. 18187
    ubiE/COQ5 methyltransferase family
    Location within SEQ ID NO 4: from 1 to 161 aa.
(D) Related Amino Acid Sequences
    Alignment No. 18188
    gi No. 124429
    % Identity 74.1
    Alignment Length 347
    Location of Alignment in SEQ ID NO 4: from 1 to 242
    Alignment No. 18189
    gi No. 1419090
    % Identity 75.7
    Alignment Length 339
    Location of Alignment in SEQ ID NO 4: from 1 to 242
    Alignment No. 18190
    gi No. 728630
    % Identity 71
    Alignment Length 62
    Location of Alignment in SEQ ID NO 4: from 181 to 242

TABLE 2

Sequence listing.

(2) INFORMATION FOR SEQ ID NO:1:
(i) SEQUENCE CHARACTERISTICS:
(A) LENGTH: 1169 base pairs
(B) TYPE: nucleic acid
(C) STRANDEDNESS: single
(D) TOPOLOGY: linear (ii) MOLECULE TYPE: DNA (ix) FEATURE:

(A) NAME/KEY: —
(B) LOCATION: 1 . . . 1169
(D) OTHER INFORMATION: / Ceres Seq. ID 1027295

(xi) SEQUENCE DESCRIPTION: SEQ ID NO:1:

TCGTTTGTGT TTTTGATTGG CGGAGAATTG GTGATAGATA AGCTTCTTCT TCCCTCTTCT
60

CAACTTGGTG GATCTGTCAT CGATGGCCTC TTTGATGCTC AACGGGGCCA TTACCTTCCC
120

CAAAGGTTTA GGTTCCCCTG GTTCCAATTT GCATGCCAGA TCGATTCCTC GGCCGACCTT
180

ACTCTCAGTT ACCCGAACCT CCACACCTAG ACTCTCGGTG GCTACTAGAT GCAGCAGCAG
240

CAGCGTGTCG TCTTCCCGGC CATCGGCGCA ACCTAGGTTC ATTCAGCACA AGAAGGAGGC
300

TTACTGGTTC TACAGGTTCT TATCCATCGT ATACGACCAT GTCATCAATC CTGGGCATTG
360

GACCGAGGAT ATGAGAGACG ACGCTCTTGA GCCAGCGGAT CTCAGCCATC CGGACATGCG
420

AGTGGTCGAT GTCGGCGGCG GAACTGGTTT CACTACTCTG GCATAGTCA AGACAGTGAA
480

GGCCAAGAAT GTGACCATTC TGGACCAGTC GCCACATCAG CTGGCCAAAG CAAAGCAAAA
540

GGAGCCGTTG AAAGAATGCA AGATCGTCGA GGGAGATGCT GAGGATCTTC CTTTTCCAAC
600

CGATTATGCT GACAGATACG TTTCTGCTGG AAGCATTGAG TACTGGCCGG ACCCGCAGAG
660

GGGAATAAGG GAAGCGTACA GGGTTCTCAA GATCGGTGGC AAAGCGTGTC TCATCGGCCC
720

TGTCTACCCA ACCTTCTGGC TCTCTCGCTT CTTTTCTGAT GTCTGGATGC TCTTCCCCAA
780

GGAGGAAGAA TACATTGAGT GGTTCAAGAA TGCCGGTTTC AAGGACGTTC AGCTCAAGAG
840

GATTGGCCCC AAGTGGTACC GTGGTGTTCG CAGGCACGGC CTTATCATGG GATATTCTGT
900

CACTGGTGTT AAACCTGCCT CCGGTGACTC TCCTCTCCAG CTTGGTCCAA AGGAAGAGGA
960

CGTAGAGAAG CCTGTCAACA ACCCCTTCTC CTTCTTGGGA CGCTTCCTCC TGGGAACTCT
1020

AGCAGCTGCC TGGTTTGTGT TAATCCCTAT CTACATGTGG ATCAAGGATC AGATCGTTCC
1080

CAAAGACCAA CCCATCTGAT CCTTCTCTTC TAGGACATGA TCATTGTATC ATTGTAAACC
1140

CCTCTTGTGG TAAAGAAAGA TTCGAGTCC (2) INFORMATION FOR SEQ ID NO:2:

TABLE 2-continued

Sequence listing.

(i) SEQUENCE CHARACTERISTICS:
(A) LENGTH: 339 amino acids
(B) TYPE: amino acid
(C) STRANDEDNESS:
(D) TOPOLOGY: linear (ii) MOLECULE TYPE: peptide (ix) FEATURE:

(A) NAME/KEY: peptide
(B) LOCATION: 1 . . . 339
(D) OTHER INFORMATION: / Ceres Seq. ID 1027296

(xi) SEQUENCE DESCRIPTION: SEQ ID NO:2:

```
Met Ala Ser Leu Met Leu Asn Gly Ala Ile Thr Phe Pro Lys Gly Leu
1               5                   10                  15

Gly Ser Pro Gly Ser Asn Leu His Ala Arg Ser Ile Pro Arg Pro Thr
            20                  25                  30

Leu Leu Ser Val Thr Arg Thr Ser Thr Pro Arg Leu Ser Val Ala Thr
            35                  40                  45

Arg Cys Ser Ser Ser Val Ser Ser Ser Arg Pro Ser Ala Gln Pro
50                  55                  60

Arg Phe Ile Gln His Lys Lys Glu Ala Tyr Trp Phe Tyr Arg Phe Leu
65                  70                  75                  80

Ser Ile Val Tyr Asp His Val Ile Asn Pro Gly His Trp Thr Glu Asp
                85                  90                  95

Met Arg Asp Asp Ala Leu Glu Pro Ala Asp Leu Ser His Pro Asp Met
            100                 105                 110

Arg Val Val Asp Val Gly Gly Gly Thr Gly Phe Thr Thr Leu Gly Ile
            115                 120                 125

Val Lys Thr Val Lys Ala Lys Asn Val Thr Ile Leu Asp Gln Ser Pro
130                 135                 140

His Gln Leu Ala Lys Ala Lys Gln Lys Glu Pro Leu Lys Glu Cys Lys
145                 150                 155                 160

Ile Val Glu Gly Asp Ala Glu Asp Leu Pro Phe Pro Thr Asp Tyr Ala
                165                 170                 175

Asp Arg Tyr Val Ser Ala Gly Ser Ile Glu Tyr Trp Pro Asp Pro Gln
            180                 185                 190

Arg Gly Ile Arg Glu Ala Tyr Arg Val Leu Lys Ile Gly Gly Lys Ala
            195                 200                 205

Cys Leu Ile Gly Pro Val Tyr Pro Thr Phe Trp Leu Ser Arg Phe Phe
210                 215                 220

Ser Asp Val Trp Met Leu Phe Pro Lys Glu Glu Glu Tyr Ile Glu Trp
225                 230                 235                 240

Phe Lys Asn Ala Gly Phe Lys Asp Val Gln Leu Lys Arg Ile Gly Pro
                245                 250                 255

Lys Trp Tyr Arg Gly Val Arg Arg His Gly Leu Ile Met Gly Tyr Ser
            260                 265                 270

Val Thr Gly Val Lys Pro Ala Ser Gly Asp Ser Pro Leu Gln Leu Gly
            275                 280                 285

Pro Lys Glu Glu Asp Val Glu Lys Pro Val Asn Asn Pro Phe Ser Phe
            290                 295                 300

Leu Gly Arg Phe Leu Leu Gly Thr Leu Ala Ala Ala Trp Phe Val Leu
305                 310                 315                 320

Ile Pro Ile Tyr Met Trp Ile Lys Asp Gln Ile Val Pro Lys Asp Gln
```

TABLE 2-continued

Sequence listing.

325                 330                 335
Pro Ile X (2) INFORMATION FOR SEQ ID NO:3:
(i) SEQUENCE CHARACTERISTICS:
(A) LENGTH: 335 amino acids
(B) TYPE: amino acid
(C) STRANDEDNESS:
(D) TOPOLOGY: linear (ii) MOLECULE TYPE: peptide (ix) FEATURE:

(A) NAME/KEY: peptide
(B) LOCATION: 1 . . . 335
(D) OTHER INFORMATION: / Ceres Seq. ID 1027297

(xi) SEQUENCE DESCRIPTION: SEQ ID NO:3:

Met Leu Asn Gly Ala Ile Thr Phe Pro Lys Gly Leu Gly Ser Pro Gly
1               5                   10                  15

Ser Asn Leu His Ala Arg Ser Ile Pro Arg Pro Thr Leu Leu Ser Val
            20                  25                  30

Thr Arg Thr Ser Thr Pro Arg Leu Ser Val Ala Thr Arg Cys Ser Ser
            35                  40                  45

Ser Ser Val Ser Ser Ser Arg Pro Ser Ala Gln Pro Arg Phe Ile Gln
50                  55                  60

His Lys Lys Glu Ala Tyr Trp Phe Tyr Arg Phe Leu Ser Ile Val Tyr
65                  70                  75                  80

Asp His Val Ile Asn Pro Gly His Trp Thr Glu Asp Met Arg Asp Asp
                85                  90                  95

Ala Leu Glu Pro Ala Asp Leu Ser His Pro Asp Met Arg Val Val Asp
            100                 105                 110

Val Gly Gly Gly Thr Gly Phe Thr Thr Leu Gly Ile Val Lys Thr Val
            115                 120                 125

Lys Ala Lys Asn Val Thr Ile Leu Asp Gln Ser Pro His Gln Leu Ala
130                 135                 140

Lys Ala Lys Gln Lys Glu Pro Leu Lys Glu Cys Lys Ile Val Glu Gly
145                 150                 155                 160

Asp Ala Glu Asp Leu Pro Phe Pro Thr Asp Tyr Ala Asp Arg Tyr Val
                165                 170                 175

Ser Ala Gly Ser Ile Glu Tyr Trp Pro Asp Pro Gln Arg Gly Ile Arg
            180                 185                 190

Glu Ala Tyr Arg Val Leu Lys Ile Gly Gly Lys Ala Cys Leu Ile Gly
            195                 200                 205

Pro Val Tyr Pro Thr Phe Trp Leu Ser Arg Phe Phe Ser Asp Val Trp
210                 215                 220

Met Leu Phe Pro Lys Glu Glu Glu Tyr Ile Glu Trp Phe Lys Asn Ala
225                 230                 235                 240

Gly Phe Lys Asp Val Gln Leu Lys Arg Ile Gly Pro Lys Trp Tyr Arg
                245                 250                 255

Gly Val Arg Arg His Gly Leu Ile Met Gly Tyr Ser Val Thr Gly Val
            260                 265                 270

Lys Pro Ala Ser Gly Asp Ser Pro Leu Gln Leu Gly Pro Lys Glu Glu
            275                 280                 285

Asp Val Glu Lys Pro Val Asn Asn Pro Phe Ser Phe Leu Gly Arg Phe
290                 295                 300

TABLE 2-continued

Sequence listing.

Leu Leu Gly Thr Leu Ala Ala Ala Trp Phe Val Leu Ile Pro Ile Tyr
305                 310                 315                 320

Met Trp Ile Lys Asp Gln Ile Val Pro Lys Asp Gln Pro Ile X
            325                 330                 335

(2) INFORMATION FOR SEQ ID NO:4:
(i) SEQUENCE CHARACTERISTICS:
(A) LENGTH: 243 amino acids
(B) TYPE: amino acid
(C) STRANDEDNESS:
(D) TOPOLOGY: linear (ii) MOLECULE TYPE: peptide (ix) FEATURE:

(A) NAME/KEY: peptide
(B) LOCATION: 1 . . . 243
(D) OTHER INFORMATION: / Ceres Seq. ID 1027298

(xi) SEQUENCE DESCRIPTION: SEQ ID NO:4:

Met Arg Asp Asp Ala Leu Glu Pro Ala Asp Leu Ser His Pro Asp Met
1                   5                   10                  15

Arg Val Val Asp Val Gly Gly Gly Thr Gly Phe Thr Thr Leu Gly Ile
                20                  25                  30

Val Lys Thr Val Lys Ala Lys Asn Val Thr Ile Leu Asp Gln Ser Pro
            35                  40                  45

His Gln Leu Ala Lys Ala Lys Gln Lys Glu Pro Leu Lys Glu Cys Lys
        50                  55                  60

Ile Val Glu Gly Asp Ala Glu Asp Leu Pro Phe Pro Thr Asp Tyr Ala
65                  70                  75                  80

Asp Arg Tyr Val Ser Ala Gly Ser Ile Glu Tyr Trp Pro Asp Pro Gln
                85                  90                  95

Arg Gly Ile Arg Glu Ala Tyr Arg Val Leu Lys Ile Gly Gly Lys Ala
                100                 105                 110

Cys Leu Ile Gly Pro Val Tyr Pro Thr Phe Trp Leu Ser Arg Phe Phe
            115                 120                 125

Ser Asp Val Trp Met Leu Phe Pro Lys Glu Glu Tyr Ile Glu Trp
        130                 135                 140

Phe Lys Asn Ala Gly Phe Lys Asp Val Gln Leu Lys Arg Ile Gly Pro
145                 150                 155                 160

Lys Trp Tyr Arg Gly Val Arg Arg His Gly Leu Ile Met Gly Tyr Ser
                165                 170                 175

Val Thr Gly Val Lys Pro Ala Ser Gly Asp Ser Pro Leu Gln Leu Gly
            180                 185                 190

Pro Lys Glu Glu Asp Val Glu Lys Pro Val Asn Asn Pro Phe Ser Phe
        195                 200                 205

Leu Gly Arg Phe Leu Leu Gly Thr Leu Ala Ala Ala Trp Phe Val Leu
    210                 215                 220

Ile Pro Ile Tyr Met Trp Ile Lys Asp Gln Ile Val Pro Lys Asp Gln
225                 230                 235                 240

Pro Ile X

TABLE 3

Alignment table.

```
Query: Pat. Appln. SEQ ID NO 1. Ceres seq_id 1027295

>gi | 124429
Score: 1323
Hsp Length: 347  Percent Identity: 74.1279069767442  Frame: 2

Alignment No. 18180 in SEQ ID NO 2

Query:  83 MASLMLNGAITF-------PKGLGSPGSNLHAR-SIPRPTLLSVTRTSTPR-LSVATRCS
            MA  MLNG              P  L   GS       PR  L     R        L   T C
Sbjct:   1 MACSMLNGVDKLALISGKTPNRLRFSGSDFTGSYKLPRLNLPPNSRNLRAKTLTTVTKCT Query:     SSSVSSSRPSAQPRFIQHKKEAYWFYRFLSIVYDHVINPGHWTEDMRDDALEPADLSHPD
            S   S RP  QPRFIQ K EA WFYRFLSIVYD  INPGHWTEDMRD ALEPADL
Sbjct:     LSA--SERPASQPRFIQNKQEAFWFYRFLSIVYDNIINPGHWTEDMRDVALEPADLNNRN Query:     MRVVDVGGGTGFTTLGIVKTVKAKNVTILDQSPHQLAKAKQKEPLKECKIVEGDAEDLPF
            M VVDVGGGTGFTTLGI K V  KNVTILDQSPHQLAKAK K PLKEC I EGDAEDLPF
Sbjct:     MLVVDVGGGTGFTTLGIIKHVDPKNVTILDQSPHQLAKAKAKKPLKECRIIEGDAEDLPF Query:     PTDYADRYVSAGSIEYWPDPQRGIREAYRVLKIGGKACLIGPVYPTFWLSRFFSDVWMLF
            PTDYADRYVSAGSIEYWPDPQRGIREAYRVLK GGKACLIGPVYPTFWLSRFF DVWMLF
Sbjct:     PTDYADRYVSAGSIEYWPDPQRGIREAYRVLKLGGKACLIGPVYPTFWLSRFFADVWMLF Query:     PKEEEYIEWFKNAGFKDVQLKRIGPKWYRGVRRHGLIMGYSVTGVKPASGDSPLQLGPKE
            PKEEEYIEWF  AGFKDVQLKRIGPKWYRGVRRHGLIMG SVTGVKPASGDSPLQLGPK
Sbjct:     PKEEEYIEWFQKAGFKDVQLKRIGPKWYRGVRRHGLIMGCSVTGVKPASGDSPLQLGPKV Query:     EDVEKPVNNPFSFLGRFLLGTLAAAWFVLIPIYMWIKDQIVPKDQPI         1096 (SEQ ID NO:
                                                                         5)
            EDV KPV  P  FL RFLLG LA     VL PIYMWIKD I PK  P              (SEQ ID NO:
                                                                         6)
Sbjct:     EDVQKPVH-PLVFLYRFLLGALASTYYVLVPIYMWIKDKIFPKGMPL          344 (SEQ ID NO:
                                                                         7)
```

DETAILED DESCRIPTION OF THE INVENTION

The invention relates to (I) polynucleotides and methods of use thereof, such as
IA. Probes & Primers;
IB. Methods of Detection & Isolation;
  B.1. Hybridization;
  B.2. Methods of Mapping;
  B.3. Southern Blotting;
  B.4. Isolating cDNA from Related Organisms;
  B.5. Isolating and/or Identifying Orthologous Genes
IC. Methods of Inhibiting Gene Expression
  C.1. Antisense
  C.2. Ribozyme Constructs;
  C.3. Co-Suppression;
  C.4. Other Methods to Inhibit Gene Expression
ID. Methods of Functional Analysis;
IE. Promoter Sequences and Their Use;
IF. UTR's and/or Intron Sequences and Their Use; and
IG. Coding Sequences and Their Use.

The specification also discloses (II) polypeptides including, without limitation, native proteins, mutants, fragments, and fusions.

The specification further discloses (III) methods of modulating polypeptide production. Examples of such methods include (i) suppressed, (ii) enhanced, and (iii) directed expression.

The application further describes (IV) gene constructs, expression vector components and (V) transformation procedures to illustrate the invention by way of examples.

The specification further describes (VI) use of polypeptides of the invention to prepare antibodies.

I. Polynucleotides

SDFs of the invention represent portions of the genome of *Arabidopsis* and/or represent mRNA expressed from that genome. The isolated nucleic acid of the invention also encompasses corresponding portions of the genome and/or cDNA complement of other organisms as described in detail below.

It is contemplated that the nucleotide sequences presented herein may contain some small percentage of errors. These errors may arise in the normal course of determination of nucleotide sequences. Sequence errors can be corrected by obtaining seeds deposited under the accession numbers cited above, propagating them, isolating genomic DNA or appropriate mRNA from the resulting plants or seeds thereof, amplifying the relevant portion of the genomic DNA or mRNA using primers having a sequence that flanks the erroneous sequence, and sequencing the amplification product.

The nucleotide sequence disclosed in Table 2 herein as representative of an SDF of the invention can be also obtained by sequencing genomic DNA from *Arabidopsis thaliana*, Wassilewskija ecotype or by sequencing cDNA obtained from mRNA from such plants as described below. This is a true breeding strain. Seeds of the plant are available from the *Arabidopsis* Biological Resource Center at the Ohio State University, under the accession number CS2360.

Starting material for cDNA synthesis for the exemplary cDNA clone having the sequence presented in Table 2 was polysomal RNA, which was isolated from the inflorescence tissues (the very top apex of the plant) of *Arabidopsis thaliana* Landsberg erecta (L. er.) that also was obtained from the *Arabidopsis* Biological Resource Center. Nine parts of the inflorescence to every part of root was used, as measured by mass. Tissue was pulverized and exposed to liquid nitrogen. Next, the sample was homogenized in the presence of detergents and then centrifuged. The debris and nuclei were removed from the sample and more detergents were added to the sample. The sample was centrifuged, the debris was removed, and the sample was applied to a 2M sucrose cushion to isolate polysomal RNA (Cox et al., "Plant Molecular Biology: A Practical Approach", pp. 1-35, Shaw ed., c. 1988 by IRL, Oxford). The polysomal RNA was used for cDNA synthesis by the methods described below.

Following preparation of the mRNAs from various tissues as described above, selection of mRNA with intact 5' ends and specific attachment of an oligonucleotide tag to the 5' end of such mRNA is performed using either a chemical or enzymatic approach. Both techniques take advantage of the presence of the "cap" structure, which characterizes the 5' end of intact mRNAs and which comprises a guanosine generally methylated once, at the 7 position.

The chemical modification approach involves the optional elimination of the 2', 3'-cis diol of the 3' terminal ribose, the oxidation of the 2', 3', -cis diol of the ribose linked to the cap of the 5' ends of the mRNAs into a dialdehyde, and the coupling of the such obtained dialdehyde to a derivatized oligonucleotide tag. Further details regarding the chemical approaches for obtaining mRNAs having intact 5' ends are disclosed in International Application No. WO96/34981 published Nov. 7, 1996.

The enzymatic approach for ligating the oligonucleotide tag to the 5' ends of mRNAs with intact 5' ends involves the removal of the phosphate groups present on the 5' ends of uncapped incomplete mRNAs, the subsequent decapping of mRNAs with intact 5' ends and the ligation of the phosphate present at the 5' end of the decapped mRNA to an oligonucleotide tag. Further details regarding the enzymatic approaches for obtaining mRNAs having intact 5' ends are disclosed in Dumas Milne Edwards J. B. (Doctoral Thesis of Paris VI University, Le clonage des ADNc complets: difficultes et perspectives nouvelles. Apports pour l'etude de la regulation de l'expression de la tryptophane hydroxylase de rat, 20 Dec. 1993), EP0 625572, and Kato et al., Gene 150:243-250 (1994).

In either the chemical or the enzymatic approach, the oligonucleotide tag has a restriction enzyme site (e.g., EcoRI sites) therein to facilitate later cloning procedures. Following attachment of the oligonucleotide tag to the mRNA, the integrity of the mRNA is then examined by performing a Northern blot using a probe complementary to the oligonucleotide tag.

For the mRNAs joined to oligonucleotide tags using either the chemical or the enzymatic method, first strand cDNA synthesis is performed using reverse transcriptase with an oligo-dT primer. In some instances, this oligo-dT primer can contain an internal tag of at least 4 nucleotides, which can be different from one preparation to another. In order to protect internal EcoRI sites in the cDNA from digestion at later steps in the procedure, methylated dCTP is used for first strand synthesis. After removal of RNA by an alkaline hydrolysis, the first strand of cDNA is precipitated using isopropanol in order to eliminate residual primers.

The second strand of the cDNA is then synthesized with a DNA polymerase, such as Klenow fragment, using a primer corresponding to the 5' end of the ligated oligonucleotide. Preferably, the primer is 20-25 bases in length. Methylated dCTP is also used for second strand synthesis in order to protect internal EcoRI sites in the cDNA from digestion during the cloning process.

Following second strand synthesis, the full-length cDNAs are cloned into a phagemid vector, such as pBlueScript™ (Stratagene). The ends of the full-length cDNAs are blunted with T4 DNA polymerase (Biolabs) and the cDNA was digested with EcoRI. Since methylated dCTP is used during cDNA synthesis, the EcoRI site present in the tag is the only hemi-methylated site; hence the only site susceptible to EcoRI digestion. In some instances, to facilitate subcloning, an Hind III adaptor is added to the 3' end of full-length cDNAs.

The full-length cDNAs are then size fractionated using either exclusion chromatography (AcA, Biosepra) or electrophoretic separation which yields 3 to 6 different fractions. The full-length cDNAs are then directionally cloned either into pBlueScript™ using either the EcoRI and SmaI restriction sites or the EcoRI and Hind III restriction sites when the Hind III adaptator is present in the full-length cDNAs. The ligation mixture is electroporated into bacteria and propagated under appropriate antibiotic selection.

Clones containing the oligonucleotide tag attached to full-length cDNAs are then selected as follows. The plasmid DNAs containing cDNA libraries made as described above are purified (e.g., by a column available from Qiagen). A positive selection of the tagged clones is performed as follows. Briefly, in this selection procedure, the plasmid DNA is converted to single stranded DNA using gene II endonuclease of the phage F1 in combination with an exonuclease (Chang et al., Gene 127:95 (1993)) such as exonuclease III or T7 gene 6 exonuclease. The resulting single stranded DNA is then purified using paramagnetic beads as described by Fry et al., Biotechniques, 13: 124 (1992.) In this procedure, the single stranded DNA is hybridized with a biotinylated oligonucleotide having a sequence corresponding to the 3' end of the oligonucleotide tag described in Example 2. Preferably, the primer has a length of 20-25 bases. Clones including a sequence complementary to the biotinylated oligonucleotide are selected by incubation with streptavidin coated magnetic beads followed by capture of the beads by magnetic selection. After capture of the positive clones, the plasmid DNA is released from the magnetic beads and converted into double stranded DNA using a DNA polymerase such as the ThermoSequenase obtained from Amersham Pharmacia Biotech. Alternatively, protocols such as the Gene Trapper kit (Gibco BRL) may be used. The double stranded DNA was then electroporated into bacteria. The percentage of positive clones having the 5' tag oligonucleotide is estimated to typically rank between 90 and 98% using dot blot analysis.

Following electroporation, the libraries are ordered in microtiter plates and sequenced.

Other methods for cloning full-length cDNA are described, for example, by Seki et al., Plant Journal 15(5): 707-720 (1998) entitled "High-efficiency cloning of Arabidopsis full-length cDNA by biotinylated Cap trapper"; Maruyama et al., Gene 138:171 (1994) entitled "Oligo-capping a simple method to replace the cap structure of eukaryotic mRNAs with oligoribonucleotides"; and WO 96/34981.

I.A. Probe & Primers

Probes and primers of the instant invention will hybridize to a polynucleotide comprising a sequence in Table 2. Though many different nucleotide sequences can encode an amino acid sequence, in some instances, the sequence of Table 2 is preferred for encoding polypeptides of the invention. However, the sequence of the probes and/or primers of the instant invention need not be identical to that in Table 2 or the complement thereof. Some variation in the sequence and length can lead to increase assay sensitivity if the nucleic acid probe can form a duplex with a target nucleotide in a sample that can be detected or isolated. The probes and/or primers of the invention can include additional nucleotides that may be helpful as a label to detect the formed duplex or for later cloning purposes.

Probe length will vary depending on the application. For use as a PCR primer, probes should be 12-40 nucleotides, preferably 18-30 nucleotides long. For use in mapping, probes should be 50 to 500 nucleotides, preferably 100-250 nucleotides long. For Southern hybridizations, probes as long as several kilobases can be used as explained below.

The probes and/or primers can be produced by synthetic procedures such as the triester method of Matteucci et al. *J. Am. Chem. Soc.* (1981) 103: 3185; or according to Urdea et al., *Proc. Natl. Acad.* 80: 7461 (1981) or using commercially available automated oligonucleotide synthesizers.

I.B. Methods of Detection & Isolation

B.1. Hybridization

Probes and/or primers can be used either for detection and/or isolation of polynucleotide sequences. Such polynucleotides are included in the subject matter of the invention. Depending on the stringency of the conditions under which these probes and/or primers are used, polynucleotides exhibiting a wide range of similarity to those in Table 2 can be detected or isolated.

"Stringency" is a function of probe length, probe composition (G+C content), and hybridization or wash conditions of salt concentration, organic solvent concentration, and temperature. Stringency is typically compared by the parameter "Tm", which is the temperature at which 50% of the complementary molecules in the hybridization are hybridized, in terms of a temperature differential from Tm. High stringency conditions are those providing a condition of Tm−5° C. to Tm−10° C. Medium stringency conditions are those providing Tm−20° C. to Tm−29° C. Low stringency conditions are those providing a condition of Tm−40° C. to Tm−48° C. The relationship of hybridization conditions to Tm (in ° C.) is expressed in the mathematical equation $$Tm=81.5-16.6(\log 10[Na+])+0.41(\% \ G+C)-(600/N) \quad (1)$$

where N is the length of the probe. This equation works well for probes 14 to 70 nucleotides in length that are identical to the target sequence. For probes of 50 nucleotides to greater than 500 nucleotides, and conditions that include an organic solvent (formamide) an alternative formulation for Tm of DNA-DNA hybrids is useful.

$$Tm=81.5+16.6 \log \{[Na+]/(1+0.7[Na+])\}+0.41(\% \ G+C)-500/L \ 0.63(\% \ \text{formamide}) \quad (2)$$

where L is the length of the probe in the hybrid (P. Tijessen, "Hybridization with Nucleic Acid Probes" in Laboratory Techniques in Biochemistry and Molecular Biology, P. C. vand der Vliet, ed., c. 1993 by Elsevier, Amsterdam). With respect to equation (2), Tm is affected by the nature of the hybrid; for DNA-RNA hybrids Tm is 10-15° C. higher than calculated, for RNA-RNA hybrids Tm is 20-25° C. higher. Most importantly for use of hybridization to identify DNA including genes corresponding to SDFs, Tm decreases about 1° C. for each 1% decrease in homology when a long probe is used (Bonner et al., *J. Mol. Biol.* 81:123 (1973)).

Equation (2) is derived under assumptions of equilibrium and therefore, hybridizations according to the present invention are most preferably performed under conditions of probe excess and for sufficient time to achieve equilibrium. The time required to reach equilibrium can be shortened by inclusion of a "hybridization accelerator" such as dextran sulfate or another high volume polymer in the hybridization buffer.

When the practitioner wishes to examine the result of membrane hybridizations under a variety of stringencies, an efficient way to do so is to perform the hybridization under a low stringency condition, then to wash the hybridization membrane under increasingly stringent conditions. With respect to wash steps preferred stringencies lie within the ranges stated above; high stringency is 5-8° C. below Tm, medium stringency is 26-29° C. below Tm and low stringency is 45-48° C. below Tm.

A number of methods known to those skilled in the art can be used with the probes and/or primers of the invention to isolate and detected polynucleotides, including, without limitation: Southerns, Northerns, Branched DNA hybridization assays, polymerase chain reaction, and variations thereof.

When using SDFs to identify orthologous genes in other species, the practitioner will preferably adjust the amount of target DNA of each species so that, as nearly as is practical, the same number of genome equivalents are present for each species examined. This prevents faint signals from species having large genomes, and thus small numbers of genome equivalents per mass of DNA, from erroneously being interpreted as lack of the presence of the corresponding gene in the genome.

A good general discussion of the factors for determining hybridization conditions is provided by Sambrook et al. (Molecular Cloning, a Laboratory Manual, 2nd ed., c. 1989 by Cold Spring Harbor Laboratory Press, Cold Spring Harbor, N.Y.; see esp., chapters 11 and 12). Additional considerations and details of the physical chemistry of hybridization are provided by G. H. Keller and M. M. Manak "DNA Probes", 2nd Ed. pp. 1-25, c. 1993 by Stockton Press, New York, N.Y.

Hybridization of one nucleic acid to another constitutes a physical property that defines the subject SDF of the invention. Also, such hybridization imposes structural limitations on the pair. For example, for a probe molecule, given that the sequence of the probe nucleic acid is known and fixed, equation (2) indicates that the combined variation in GC content of the target DNA and mismatch between the probe and the hybridizing DNA is determined for any given hybridization buffer composition and Tm.

The probes and/or primers of the instant invention can be used to detect or isolate nucleotides that are "identical" to the probes or primers. Two nucleic acid sequences or polypeptides are said to be "identical" if the sequence of nucleotides or amino acid residues, respectively, in the two sequences is the same when aligned for maximum correspondence as described below. The term "complementary to" is used herein to mean that the sequence can form a Watson-Crick base pair with a reference polynucleotide sequence. Complementary sequences can include nucleotides, such as inosine, that do not disrupt Watson-Crick base pairing, but also do not contribute to the pairing.

Optimal alignment of sequences for comparison may be conducted by the local homology algorithm of Smith and Waterman Add. APL. Math. 2:482 (1981), by the homology alignment algorithm of Needleman and Wunsch, *J. Mol. Biol.* 48:443 (1970), by the search for similarity method of Pearson and Lipman, *Proc. Natl. Acad. Sci.* (USA) 85: 2444 (1988), by computerized implementations of these algorithms (GAP, BESTFIT, BLAST, PASTA, and TFASTA in the Wisconsin Genetics Software Package, Genetics Computer Group (GCG), 575 Science Dr., Madison, Wis.), or by inspection. Given that two sequences have been identified for comparison, GAP and BESTFIT are preferably employed to determine their optimal alignment. Typically, the default values of 5.00 for gap weight and 0.30 for gap weight length are used.

The probes and/or primers or the invention can also be used to detect and/or isolate polynucleotides exhibiting at least 80% sequence identity with the sequence of Table 2 or fragments thereof. "Percentage of sequence identity" is determined by comparing two optimally aligned sequences over a comparison window, wherein the portion of the polynucleotide sequence in the comparison window may comprise additions or deletions (e.g., gaps or overhangs) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" between polynucleotide or polypeptide sequences refers to polynucleotide or polypeptide comprising a sequence that has at least 80% sequence identity, preferably at least 85%, more preferably at least 90% and most preferably at least 95%, even more preferably, at least 96%, 97%, 98% or 99% sequence identity compared to a reference sequence using the programs.

Isolated polynucleotides within the scope of the invention also include allelic variants of the specific sequence presented in Table 2. An "allelic variant" is a sequence that is a variant from that of the SDF, but represents the same chromosomal locus in the organism. In addition to those that occur by normal genetic variation in a population and perhaps fixed in the population by standard breeding methods, allelic variants can be produced by genetic engineering methods. A preferred allelic variant is one that is found in a naturally occurring plant, including a laboratory cultivar or ecotype. Allelic variants are either silent or expressed. A silent allele is one that does not affect the phenotype of the organism. An expressed allele results in a detectable change in the phenotype of the trait represented by the locus. Alleles can occur in any portion of the genome, including regulatory regions as well as structural genes.

As is apparent from the above explanation, the SDFs of the invention encompass minor variation in the nucleotide sequence and amino acid sequences presented in Table 2. With respect to nucleotide sequences, degeneracy of the genetic code provides the possibility to substitute at least one base of the base sequence of a gene by a different base without causing the amino acid sequence of the polypeptide produced from the gene to be changed. Hence, the DNA of the present invention may also have any base sequence that has been changed from a the sequence in Table 2 by substitution in accordance with degeneracy of the genetic code. References describing codon usage include: Carels et at., *J. Mol. Evol.* 46: 45 (1998) and Fennoy et at., *Nucl. Acids Res.* 21(23): 5294 (1993).

B.2. Mapping

The isolated DNA of the invention can be used to physically map particular clones representing *Arabidopsis* DNA to the *Arabidopsis* genome. In this embodiment of the invention, the cloned DNA of interest is hybridized to a panel of SDFs of the invention.

First, SDFs of the invention are assigned to Bacterial Artificial Chromosome (BAC) or Yeast Artificial Chromosome (YAC) clones, preferably clones that have been ordered as a contig library. Then, the SDFs are arrayed on a filter, preferably in a logical order that reflects their physical arrangement in the genome. That is, SDFs that are proximate to each other in the genome are also located next to each other on the filter and the ordering of the SDFs in the genome is similarly reflected on the filter. Hybridization of the particular DNA to particular SDFs thus identifies those BAC(s) or YAC(s) that contain DNA having a nucleotide sequence similar or identical to that of the particular DNA of interest. Thus, the DNA of interest is quickly located on the physical map of the *Arabidopsis* genome.

If the DNA of interest is known to provide, or at least to influence, a particular phenotypic trait, then the phenotypic trait is also thus quickly ordered on the physical map and linkage is established to other mapped traits.

The cloned DNA of the invention can also be used to establish markers for genetic traits. The SDFs can be used as probes to identify polymorphisms in the genome of ecotypes, preferably recombinant inbred ecotypes, having different alleles of at least two particular traits. Then, genotyping of these parental ecotypes can be performed and the genotypes compared to F1 recombinants between the traits. The frequency of recombination between the polymorphisms and between the phenotypic traits is analyzed to identify those polymorphisms that are most often, preferably always, transmitted together with the phenotypic trait.

Use of recombinant inbred lines for genetic mapping in *Arabidopsis* is described by Alonso-Blanco et al., Methods in Molecular Biology, vol. 82, "*Arabidopsis* Protocols", pp. 137-146, J. M. Martinez-Zapater and J. Salinas, eds., c. 1998 by Humana Press, Totowa, N.J.

In the most preferred instance, the relevant polymorphism will be found within the sequence of an SDF and this sequence will be the basis for designing differential probes for different alleles. For example, sequence mismatches can be exploited to provide diagnostics based on polymerase chain reaction or ligation-amplification approaches (K. J. Williams et al., *Genome* 39:7, 798 (1996) and R. A. Guilfoyle, *Nucleic Acids Res.* 25:9, 1854 (1997)). Tandem repeats of simple sequences or variable number tandem repeats and the like can be identified by hybridization or polymerase chain reaction assays. (U.S. Pat. No. 5,766,847; U. H. Refseth et al., *Electrophoresis* 18:9, 1519 (1997)). Hybridization to arrays of oligonucleotides can be used to scan multiple alleles of a plurality of loci. (U.S. Pat. Nos. 5,445,934 and 5,410,270 and WO9535505).

B.3 Southern Blot Hybridization

Hybridization techniques using the sequence from Table 2 as a probe or primer are a means of detecting target polynucleotides in a sample. These assays can be used to determine if transgenic plants, seeds, or host cells comprise the gene or sequence of interest and therefore will exhibit the trait, phenotype, etc. of interest.

In addition, the hybridization of the SDFs of the invention to nucleic acids obtained from other organisms can be used to identify orthologous genes from other species and/or additional members of gene families either in the same or different species. In regard to identifying genes in other species, a Southern blot of genomic DNA provides description of isolated DNA fragments that comprise the orthologous genes or additional members of the gene families. That is, given such data, one of ordinary skill in the art could distinguish the isolated DNA fragments by their size together with the restriction sites at each end and by the property of hybridizing with the SDF probe under the stated conditions.

Southern blots can also be used to generate a map of the portion of the genome of the other species that includes the DNA corresponding to the SDF. Such a map provides additional information about the relative position of restriction sites within fragments, further distinguishing mapped DNA from the remainder of the genome.

At least two single digestions of the genomic DNA by restriction enzymes, and a double digestion with both, are preferable to make a simple map. Preferably additional enzymes and their combinations will be used to generate a map having more detail. In the event that ambiguities are found in the simple map, they can usually be resolved by repeating the experiment using additional enzymes. Digestions with a single enzyme, especially together with hybridization to a probe sequence, can be used to at least distinguish individual restriction fragments from the remainder of the genome.

Probes for Southern blotting can range in size from 15 to 20 nucleotides to several thousand nucleotides. More preferably, the probe is 100 to 1000 nucleotides long for identifying members of a gene family when it is found that repetitive sequences would complicate the hybridization. For identifying an entire corresponding gene in another species, the probe is more preferably the length of the gene, typically 2000 to 10,000 nucleotides, but probes 50-1,000 nucleotides long might be used. Some genes, however, might require probes up to 15,000 nucleotides long to span their lengths. In such instances, overlapping probes spanning the desired length can be used.

Also, while it is preferred that the probe be homogeneous with respect to its sequence, that is not necessary. For example, as described below, a probe representing members of a gene family having diverse sequences can be generated using PCR to amplify genomic DNA or RNA templates using primers derived from SDFs that include sequences that define the gene family.

For identifying corresponding genes in another species, the probe for Southern blotting most preferably would be the genomic copy of the probe gene. This allows all elements of the gene to be identified in the other species. The next most preferable probe is a cDNA spanning the entire coding sequence, which allows all of the mRNA-coding portion of the gene to be identified; in this case it can occur that some introns in the gene might be missed. Probes for Southern blotting can be easily generated from SDFs by making primers having the sequence at the ends of the SDF and using *Arabidopsis* genomic DNA as a template. In instances where the SDF includes sequence conserved among species, primers including the conserved sequence can be applied to PCR using genomic DNA from a species of interest to obtain a probe. Similarly, if the SDF includes a domain of interest, that portion of the SDF can be used to make primers and the appropriate template DNA used to make a probe for genes including the domain. Alternatively, the PCR products can be resolved, for example by gel electrophoresis, and cloned and/or sequenced. In this manner, the variants of the domain among members of a gene family, both within and across species, can be examined.

B.4 Isolating DNA from Related Organisms

The SDFs of the invention can be used to isolate the corresponding DNA from other organisms. Either cDNA or genomic DNA can be isolated. For isolating genomic DNA, a lambda, cosmid or YAC genomic library from the plant of interest can be constructed using standard molecular biology techniques as described in detail by Sambrook et al. 1989 (Molecular cloning: A laboratory manual, 2nd ed. Cold Spring Harbor Laboratory Press, New York) and by Ausubel et al. 1992 (Current Protocols in Molecular Biology, Greene Publishing, New York).

To screen a phage library recombinant lambda clones are plated out in appropriate bacterial medium using an appropriate *E. coli* host strain. The resulting plaques are lifted from the plates using nylon or nitrocellulose filters. The plaque lifts are processed through denaturation, neutralization, and washing treatments following the standard protocols outlined by Ausubel et al. (1992). The plaque lifts are hybridized to either radioactively labeled or non-radioactively labeled SDF DNA at room temperature for about 16 hours usually in the presence of 50% formamide and 5×SSC (sodium chloride and sodium citrate) buffer and blocking reagents. The plaque lifts are then washed at 42° C. with 1% Sodium Dodecyl Sulfate (SDS) and at a particular concentration of SSC. The SSC concentration to be used is dependent upon the stringency at which the hybridization was observed in initial Southern blot analysis performed. For example, if a hybridizing fragment can be observed under medium stringency (e.g., Tm−20° C.), then this condition is maintained or preferably adjusted to a less stringent condition (e.g., Tm−30° C.) to wash the plaque lifts. The plaque lifts are exposed to X-ray films to detect the positive clones, which are then subsequently isolated for purification using the same general protocol outlined above. Once the clone is purified, restriction analysis can be done to narrow the region corresponding to the gene of interest. The restriction analysis and succeeding subcloning steps can be done using procedures described by, for example Sambrook et al. (1989) cited above.

To screen a YAC library, the procedures outlined for the lambda library are essentially similar except the YAC clones are harbored in bacterial colonies. The YAC clones are plated out at reasonable density on nitrocellulose or nylon filters supported by appropriate bacterial medium in petri plates. Following the growth of the bacterial clones, the filters are then processed through the denaturation, neutralization, and washing steps following the procedures of Ausubel et al. 1992. The same hybridization procedures for lambda library screening are followed.

To isolate cDNA, similar procedures using appropriately modified vectors are employed. For instance, the library can be constructed in a lambda vector appropriate for cloning cDNA such as λgt11. Alternatively, the cDNA library can be made in a plasmid vector. cDNA for cloning can be prepared by any of the methods known in the art, but is preferably prepared as described above. Preferably a cDNA library will include a high proportion of full-length clones.

B.5. Isolating and/or Identifying Orthologous Genes

Probes and primers of the invention can be used to identify and/or isolate polynucleotides related to that in Table 2. Related polynucleotides are those that are native to other plant organisms and exhibit either similar sequence or encode polypeptides with similar biological activity. One specific example is an orthologous gene, a gene that has a high degree of sequence similarity, often along the entire length of the coding portion of the gene, and also encodes a gene product that performs a similar function in the organism. Orthologous genes are distinguished from homologous genes in that homologous genes share only sequence similarity and then often only in a portion of the sequence, which usually represents a functional domain such as a tyrosine kinase activity, a DNA binding domain, or the like. The degree of identity is a function of evolutionary separation and, in closely related species, the degree of identity can be 98 to 100%. The amino acid sequence of a protein encoded by an orthologous gene can be as little as 75% identical, but tends to be at least 80% identical, more preferably at least 90%, most preferably at least 95% identical to the amino acid sequence of the reference protein.

For finding orthologous genes, the probes are hybridized to nucleic acids from a species of interest under low stringency conditions and blots are then washed under conditions of increasing stringency. It is preferable that the wash stringency be such that sequences that are 85 to 100% identical will hybridize. More preferably, sequences 90 to 100% identical will hybridize and most preferably only sequences greater than 95% identical will hybridize. The low stringency condition is preferably one where sequences containing as much as 40-45% mismatches will be able to hybridize. This condition is established by Tm−40° C. to Tm−48° C. (see below). One of ordinary skill in the art will recognize that, due to degeneracy in the genetic code, amino acid sequences that are identical can be encoded by DNA sequences as little as 67% identical. Thus, it is preferable to make an overlapping series of shorter probes, on the order of 24 to 45 nucleotides, and individually hybridize them to the same arrayed library to avoid the problem of degeneracy introducing large numbers of mismatches. As evolutionary divergence increases, genome sequences also tend to diverge. Thus, one of skill will recognize that searches for orthologous genes between more divergent species will require the use of lower stringency conditions compared to searches between closely related species. Also, degeneracy is more of a problem for searches in the genome of a species more distant evolutionarily from the species that is the source of the SDF probe sequences.

Therefore the method described in Bouckaert et at, U.S. Ser. No. 60/121,700, filed Feb. 25, 1999, herewith included by reference, can be applied to the SDFs of the present invention to isolate related genes from plant species which do not hybridize to the sequence of Table 2.

Identification of the relationship of genomic sequences amongst plant species can be done by comparing the amino acid sequences corresponding to the SDFs of the present invention with amino acid sequences of other SDFs, such as those listed in the tables of U.S. patent application Ser. No. 09/940,255 or U.S. patent application Ser. No. 09/940,258. These applications are hereby expressly incorporated by reference.

The SDFs of the invention can also be used as probes to search for genes that are related to the SDF within a species. Such related genes are typically considered to be members of a "gene family." In such a case, the sequence similarity will often concentrated into one or a few portions of the sequence. The portions of similar sequence that define the gene family typically encode a portion of a protein or RNA that has an enzymatic or structural function. The degree of identity in the amino acid sequence of the domain that defines the gene family is preferably at least 70%, more preferably 80 to 95%, most preferably 85 to 99%. To search for members of a gene family within a species, a "low stringency" hybridization is usually performed, but this will depend upon the size, distribution and degree of sequence divergence of domains that define the gene family. SDFs encompassing regulatory regions can be used to identify "coordinately expressed" genes by using the regulatory region portion of the SDF as a probe.

In the instances where the SDFs are identified as being expressed from genes that confer a particular phenotype, then the SDFs can also be used as probes to assay plants of different species for those phenotypes.

In the case of polynucleotides used to inhibit expression of an endogenous gene, the introduced sequence need not be perfectly identical to a sequence of the target endogenous gene. The introduced polynucleotide sequence will typically be at least substantially identical (as determined below) to the target endogenous sequence.

I.C. Methods to Inhibit Gene Expression

C.1 Antisense

The polynucleotide SDF in Table 2 represents, amongst others, a sequence that is expressed in *Arabidopsis*. Thus, the invention includes antisense constructs based on this sequence to inhibit transcription and/or translation of said SDFs. To accomplish this, a polynucleotide segment from the desired gene is operably linked to a promoter such that the antisense strand of RNA will be transcribed.

The segment to be introduced generally will be substantially identical to at least a portion of the endogenous gene or genes to be repressed. The sequence, however, need not be perfectly identical to inhibit expression. Further, the antisense product may hybridize to the untranslated region instead of or in addition to the coding portion of the gene. The vectors of the present invention can be designed such that the inhibitory effect applies to other proteins within a family of genes exhibiting homology or substantial homology to the target gene.

For antisense suppression, the introduced sequence also need not be full length relative to either the primary transcription product or fully processed mRNA. Generally, higher sequence identity can be used to compensate for the use of a shorter sequence. Furthermore, the introduced sequence need not have the same intron or exon pattern, and homology of non coding segments may be equally effective. Normally, a sequence of between about 30 or 40 nucleotides and the full length of the transcript should be used, though a sequence of at least about 100 nucleotides is preferred, a sequence of at least about 200 nucleotides is more preferred, and a sequence of at least about 500 nucleotides is especially preferred.

C.2. Ribozymes

It is also contemplated that gene constructs representing ribozymes and based on the SDF in Table 2 are an object of the invention. Ribozymes can also be used to inhibit expression of genes by suppressing the translation of the mRNA into a polypeptide. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA cleaving activity upon them, thereby increasing the activity of the constructs.

A number of classes of ribozymes have been identified. One class of ribozymes is derived from a number of small circular RNAs, which are capable of self cleavage and replication in plants. The RNAs replicate either alone (viroid RNAs) or with a helper virus (satellite RNAs). Examples include RNAs from avocado sunblotch viroid and the satellite RNAs from tobacco ringspot virus, luceme transient streak virus, velvet tobacco mottle virus, solanum nodiflorum mottle virus and subterranean clover mottle virus. The design and use of target RNA specific ribozymes is described in Haseloff et al. *Nature,* 334:585 (1988).

Like the antisense constructs above, the ribozyme sequence portion necessary for pairing need not be identical the target nucleotides to be cleaved, nor identical to the sequence in Table 2. Generally, the sequence in the ribozyme capable of binding to the target sequence exhibits substantial sequence identity the sequence in Table 2 or the complement thereof or to a portion of said sequence or complement. Further, the ribozyme sequence also need not be full length relative to either the primary transcription product or fully processed mRNA. The ribozyme can be equally effective in inhibiting mRNA translation by cleaving either in the untranslated or coding regions. Generally, higher sequence identity can be used to compensate for the use of a shorter sequence. Furthermore, the introduced sequence need not have the same intron or exon pattern, and homology of non-coding segments may be equally effective.

C.3. Sense Suppression

Another method of suppression is by introducing an exogenous copy of the gene to be suppressed. Introduction of expression cassettes in which a nucleic acid is configured in the sense orientation with respect to the promoter has been shown to be an effective means by which to block the transcription of target genes. For an example of the use of this method to modulate expression of endogenous genes see, Napoli et al., *The Plant Cell* 2:279 (1990), and U.S. Pat. Nos. 5,034,323; 5,231,020; and 5,283,184. Generally, where inhibition of expression is desired, some transcription of the introduced sequence occurs. The effect may occur where the introduced sequence contains no coding sequence per se, but comprises only intron or untranslated sequences homologous to sequences present in the primary transcript of the endogenous sequence. The introduced sequence generally will be substantially identical to the endogenous sequence intended to be repressed. The minimal identity will typically be greater than about 65%, but a higher identity might exert a more effective repression of expression of the endogenous sequences. Substantially greater identity of more than about 80% is preferred, though about 95% to absolute identity would be most preferred. As with antisense regulation, the effect would likely apply to any other proteins within a similar family of genes exhibiting homology or substantial homology to the suppressing sequence.

C.4. Other Methods to Inhibit Gene Expression

Yet another means of suppressing gene expression is to insert a polynucleotide into the gene of interest to disrupt transcription or translation of the gene. Low frequency homologous recombination can be used to target a polynucleotide insert to a gene by flanking the polynucleotide insert with sequences that are substantially similar to the gene to be disrupted. The sequence from Table 2, fragments thereof, and substantially similar sequence thereto can be used for homologous recombination.

In addition, random insertion of polynucleotides into a host cell genome can also be used to disrupt the gene of interest. Azpiroz-Leehan et al., *Trends in Genetics* 13:152 (1997). In this method, screening for clones from a library containing random insertions is preferred to identifying those that have polynucleotides inserted into the gene of interest. Such screening can be performed using probes and/or primers described above based on the sequence from Table 2, fragments thereof, and substantially similar sequence thereto. The screening can also be performed by selecting clones or R1 plants having a desired phenotype.

I.D. Methods of Functional Analysis

The constructs described in the methods under I.C. above can be used to determine the function of the polypeptide encoded by the gene that is targeted by the constructs.

Down regulating the transcription and translation of the targeted gene, the host cell or organisms, such as a plant, may produce phenotypic changes as compared to a wild-type cell or organism. In addition, in vitro assays can be used to determine if any biological activity, such as calcium flux, DNA transcription, nucleotide incorporation, etc., are being modulated by the down-regulation of the targeted gene.

I.E. Promoters

The SDFs of the invention are also useful as structural or regulatory sequences in a construct for modulating the expression of the corresponding gene in a plant or other organism, e.g. a symbiotic bacterium. For example, promoter sequences represented in Table 2 of any priority patent application can be useful in directing expression of coding sequences either as constitutive promoters or to direct expression in particular cell types, tissues, or organs.

The term "promoter" refers to a region or sequence determinants located upstream or downstream from the start of transcription and which are involved in recognition and binding of RNA polymerase and other proteins to initiate transcription. A "plant promoter" is a promoter capable of initiating transcription in plant cells. Such promoters need not be of plant origin, for example, promoters derived from plant viruses, such as the CaMV35S promoter or from *Agrobacterium tumefaciens* such as the T-DNA promoters, can be used in the present invention. Typical constitutive promoters of plant origin such as the promoter of the cowpea trypsin inhibitor gene can be utilized. Typical examples of temporal and/or tissue specific promoters of plant origin, which can be used with the polynucleotides of the present invention, are: PTA29, a promoter which is capable of driving gene expression specifically in tapetum and only during anther development (Koltonow et al., *Plant Cell* 2:1201 (1990); RCc2 and RCc3, promoters that direct root-specific gene expression in rice (Xu et al., *Plant Mol. Biol.* 27:237 (1995); TobRB27, a root-specific promoter from tobacco (Yamamoto et al., *Plant Cell* 3:371 (1991)).

By "specific promoters" is meant a promoter having a high preference for driving gene expression in the specified tissue and/or at the specified time during the concerned tissue or organ development. By "high preference is meant at least 3-fold, preferably 5-fold, more preferably at least 10-fold, still more preferably at least 20-fold, 50-fold or 100-fold increase in expression in the desired tissue over the expression in any undesired tissue.

A typical example of an inducible promoter, which can be utilized with the polynucleotides of the present invention, is PARSK1, the promoter from the *Arabidopsis* gene encoding a serine-threonine kinase enzyme that is induced by dehydration, abscissic acid and sodium chloride (Wang and Goodman, *Plant J.* 8:37 (1995)).

With respect to the SDFs of the present invention a promoter is likely to be a relatively small portion of a genomic DNA (gDNA) sequence located in the first 2000 nucleotides upstream from an initial exon identified in a gDNA sequence or initial "ATG" or methionine codon in a cDNA or mRNA sequence. Such promoters are more likely to be found in the first 1000, most likely within the first 500 nucleotides upstream of an initial ATG or methionine codon of a cDNA sequence. The portions of a particular gDNA sequence that function as a promoter in a plant cell will preferably be found to hybridize at medium or high stringency to gDNA sequences presented in Table 2 of any priority patent application.

Promoters are generally modular in nature. Short DNA sequences representing binding sites for proteins can be separated from each other by intervening sequences of varying length. For example, within a particular functional module protein binding sites may be constituted by regions of 5 to 60, preferably 10 to 30, more preferably 10 to 20 nucleotides. Within such binding sites, there are typically 2 to 6 nucleotides that specifically contact amino acids of the nucleic acid binding protein. The protein binding sites are usually separated from each other by 10 to several hundred nucleotides, typically by 15 to 150 nucleotides, often by 20 to 50 nucleotides. DNA binding sites in promoter elements often display dyad symmetry in their sequence. Often elements binding several different proteins, and/or a plurality of sites that bind the same protein, will be combined in a region of 100 to 1000 basepairs.

Elements that have transcription regulatory function can be isolated from their corresponding endogenous gene, or the desired sequence can be synthesized, and recombined in constructs to direct expression of a structural gene in a desired tissue-specific, temporal-specific or other desired manner of inducibility or suppression. When hybridizations are performed to identify or isolate elements of a promoter by hybridization to the long sequences presented in Table 2 of any priority patent application, conditions should be adjusted to account for the above-described nature of promoters. For example short probes, constituting the element sought, should be used under low temperature and/or high salt conditions. When long probes, which might include several promoter elements are used, low to medium stringency conditions are preferred when hybridizing to promoters across species.

Promoters can consist of a "basal promoter" that functions as a site for assembly of a transcription complex comprising an RNA polymerase, for example RNA polymerase II. A typical transcription complex will include additional factors such as TFIIB, TFIID, and TFIIE. Of these, TFIID appears to be the only one to bind DNA directly. Basal promoters frequently include a "TATA box" element usually located between 20 and 35 nucleotides upstream from the site of initiation of transcription. Basal promoters also sometimes include a "CCAAT box" element (typically a sequence CCAAT) and/or a GGGCG sequence, usually located between 40 and 200 nucleotides, preferably 60 to 120 nucleotides, upstream from the start site of transcription.

The promoter might also contain one or more "enhancers" and/or "suppressors" that function as binding sites for additional transcription factors that have the function of modulating the level of transcription with respect to tissue specificity of transcription, transcriptional responses to particular environmental or nutritional factors, and the like.

If a nucleotide sequence of the SDF, or part of said SDF, functions as a promoter or portion of a promoter, then nucleotide substitutions, insertions or deletions that do not substantially affect the binding of relevant DNA binding proteins would be considered equivalent to the exemplified nucleotide sequence. It is envisioned that there are instances where it is desirable to decrease the binding of relevant DNA binding proteins to "silence" or "down-regulate" a promoter, or conversely to increase the binding of relevant DNA binding proteins to "enhance" or "up-regulate" a promoter. In such instances, polynucleotides representing changes to the nucleotide sequence of the DNA-protein contact region by insertion of additional nucleotides, changes to identity of relevant nucleotides, including use of chemically-modified bases, or deletion of one or more nucleotides are considered encompassed by the present invention.

Promoter function can be assayed by methods known in the art, preferably by activity of a reporter gene operatively linked to the sequence being tested for promoter function. Examples of reporter genes include those encoding luciferase, green fluorescent protein, GUS, neo, cat, and bar.

I.F. UTRs and Junctions

Additionally, polynucleotides comprising untranslated (UTR) sequences are within the scope of the invention. Such UTR sequences include introns and 5' or 3' untranslated regions, (5' UTRs or 3' UTRs). Fragments of the sequence shown in Table 2 can comprise UTRs and introns or intron-exon junctions.

These portions of SDFs, especially UTRs, can have regulatory functions related to, for example, translation rate and mRNA stability. Thus, these portions of SDFs can be isolated for use as elements of gene constructs for expression of polynucleotides encoding desired polypeptides.

Also, introns of genomic DNA segments might have regulatory functions. Sometimes enhancer or suppressor elements are found within introns or within promoter regions. Also, elements related to stability of heteronuclear RNA and efficiency of transport to the cytoplasm for translation can be found in intron elements. Thus, these segments can also find use as elements of expression vectors intended for their use to transform plants.

Just as with promoters, introns and other UTR sequences and intron/exon junctions can vary from that shown in Table 2. Such changes from the sequence preferably will not affect the regulatory activity of the UTRs or intron sequences on expression, transcription, or translation. However, in some instances, down-regulation of such activity may be desired to modulate traits or phenotypic or in vitro activity.

I.G. Coding Sequences

Isolated polynucleotides of the invention can include coding sequences that encode polypeptides comprising an amino acid sequence encoded by the sequence in Table 2 or an amino acid sequence presented in Table 2.

A nucleotide sequence "encodes" a polypeptide if a cell (or a cell free in vitro system) expressing that nucleotide sequence produces a polypeptide having the recited amino acid sequence when the nucleotide sequence is transcribed and the primary transcript is subsequently processed and translated by a host cell (or a cell free in vitro system) harboring the nucleic acid. Thus, an isolated nucleic acid that "encodes" a particular amino acid sequence can be a genomic sequence comprising exons and introns or a cDNA sequence that represents the product of splicing thereof. An isolated nucleic acid "encoding an amino acid sequence" also encompasses heteronuclear RNA, which contains sequences that are spliced out during expression, and mRNA, which lacks those sequences.

Coding sequences can be constructed using chemical synthesis techniques or by isolating coding sequences or by modifying such synthesized or isolated coding sequences as described above.

In addition to encoding the polypeptide sequences of Table 2, which are native to *Arabidopsis*, the isolated polynucleotides can encode mutants, fragments, and fusions of those native proteins. Such polypeptides are described below.

As noted above, the number of substitutions, deletions or insertions is preferably less than 20%, more preferably less than 15%; even more preferably less than 10%, 5%, 3% or 1% of the number of nucleotides comprising a particularly exemplified sequence. It is generally expected that non-degenerate nucleotide sequence changes that result in 1 to 10, more preferably 1 to 5 and most preferably 1 to 3 amino acid insertions, deletions or substitutions will not greatly affect the function of an encoded polypeptide. The most preferred embodiments are those wherein 1 to 20, preferably 1 to 10, most preferably 1 to 5 nucleotides are added to, deleted from and/or substituted in the sequence specifically disclosed in Table 2.

Insertions or deletions in polynucleotides intended to be used for encoding a polypeptide should preserve the reading frame. This consideration is not so important in instances when the polynucleotide is intended to be used as a hybridization probe.

II. Polypeptides

Polypeptides within the scope of the invention include both native proteins as well as mutants, fragments, and fusions thereof Polypeptides of the invention are those encoded by any of the six reading frames of the sequence shown in Table 2, preferably encoded by the three frames reading in the 5' to 3' direction of the sequences as shown.

Native polypeptides include the proteins encoded by the sequence shown in Table 2. Such native polypeptides include those encoded by allelic variants.

Variants, including mutants, will exhibit at least 80% sequence identity to those native polypeptides of Table 2. Sequence identity is used for polypeptides as defined above for polynucleotides. More preferably, the variants will exhibit at least 85% sequence identity; even more preferably, at least 90% sequence identity; more preferably at least 95%, 96%, 97%, 98%, or 99% sequence identity. "Fragments" of polypeptide or "portions" of polypeptides will exhibit similar degrees of identity to the relevant portions of the native polypeptide. Fusions will exhibit similar degrees of identity in that portion of the fusion represented by the variant of the native peptide.

Furthermore, variants will exhibit at least one of the functional properties of the native protein. Such properties include, without limitation, protein interaction, DNA interaction, biological activity, immunological activity, receptor binding, signal transduction, transcription activity, growth factor activity, secondary structure, three-dimensional structure, etc. As to properties related to in vitro or in vivo activities, the variants preferably exhibit at least 60% of the activity of the native protein; more preferably at least 70%, even more preferably at least 80%, 85%, 90% or 95% of at least one activity of the native protein.

II.A. Mutants, Fragments, and Fusions

Generally, mutants, fragments, or fusions of the polypeptides encoded by the maximum length sequence (MLS) can exhibit at least one of the activities of the identified domains and/or related polypeptides described in Sections (C) and (D) of Table 1 corresponding to the MLS of interest.

II.A.(I) Mutants

A type of mutant of the native polypeptides comprises amino acid substitutions. "Conservative substitutions" are preferred to maintain the function or activity of the polypeptide. Such substitutions include conservation of charge, polarity, hydrophobicity, size, etc. For example, one or more amino acid residues within the sequence can be substituted with another amino acid of similar polarity that acts as a functional equivalent, for example providing a hydrogen bond in an enzymatic catalysis. Substitutes for an amino acid within an exemplified sequence are preferably made among the members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Within the scope of sequence identity described above, a polypeptide of the invention may have additional individual amino acids or amino acid sequences inserted into the polypeptide in the middle thereof and/or at the N-terminal and/or C-terminal ends thereof. Likewise, some of the amino acids or amino acid sequences may be deleted from the polypeptide. Amino acid substitutions may also be made in the sequences; conservative substitutions being preferred.

One preferred class of mutants are those that comprise (1) the domain of a MLS-encoded polypeptide and/or (2) residues conserved between the MLS-encoded polypeptide and related polypeptides of the MLS. For this class of mutants, the MLS-encoded polypeptide sequence is changed by insertion, deletion, or substitution at positions flanking the domain and/or conserved residues.

Another class of mutants includes those that comprise a MLS-encoded polypeptide sequence that is changed in the domain or conserved residues by a conservative substitution.

Yet another class of mutants includes those that lack one the in vitroin vitro activities, or structural features of the MLS-encoded polypeptides. One example is dominant negative mutants. A dominant negative mutant can comprise a MLS-encoded polypeptide sequence with non-conservative changes in the domain or conserved residues.

II.A.(2) Fragments

Fragments of particular interest are those that comprise the domain identified for the polypeptides encoded by MLS of the instant invention and mutants thereof. Also, fragments that comprise a region of residues conserved between the MLS-encoded polypeptides and its related polypeptides.

II.A.(3) Fusions

Of interest are chimeric polypeptides comprising (1) a fragment of the MLS-encoded polypeptide or mutants thereof of interest and (2) a fragment of a polypeptide comprising the same domain. An example of such a chimeric polypeptide is, an AP2 helix encoded by a MLS of the invention fused to a second AP2 helix from an ANT protein, which comprises two AP2 helices. The present invention also encompasses fusions of MLS-encoded polypeptides, mutants, or fragments thereof fused with related proteins or fragments thereof.

Definition of Domains

The polypeptides of the invention can possess identifying domains as indicated in Table 1. Domains are fingerprints or signatures that can be used to characterize protein families and/or motifs. Such fingerprints or signatures can comprise conserved (1) primary sequence, (2) secondary structure, and/or (3) three-dimensional conformation. Generally, each domain has been associated with either a family of proteins or a motif. Typically, these families and motifs have been correlated with specific in vitro and/or in vivo activities. Detailed descriptions of the domains, associated families & motifs, and correlated activities of the polypeptides of the instant invention are described below. Usually, the polypeptides with designated domain(s) can exhibit at least one activity that is exhibited by any polypeptide that comprises the same domain(s).

Specific domains within the MLS-encoded polypeptides are indicated by reference Table 1. In addition, the domains with the MLS-encoded-polypeptide can be defined by the region that exhibits at least 70% sequence identity with the consensus sequences listed in the detailed description of each of the domains provided below. The protein domain descriptions given below are obtained from Prosite, (expasy.ch/prosite/) (contains 1030 documentation entries that describe 1366 different patterns, rules and profiles/matrices), and Pfam, (pfam.wustl.edu/browse.shtml).

The particular sequences of identified SDFs are provided in Table 2. One of ordinary skill in the art, having this data, can obtain cloned DNA fragments, synthetic DNA fragments or polypeptides constituting desired sequences by recombinant methodology known in the art.

Ubie/COQ5 Methyltransferase Family Signatures

The following methyltransferases have been shown (Lee et al., *J. Bacteriol.* 179:1748-1754 (1997)) to share regions of similarities: (1) *Escherichia coli* ubiE, which is involved in both ubiquinone and menaquinone biosynthesis and which catalyzes the S-adenosylmethionine dependent methylation of 2-polyprenyl-6-methoxy-1,4-benzoquinol into 2-polyprenyl-3-methyl-6-methoxy-1,4-benzoquinol and of demethylmenaquinol into menaquinol, (2) Yeast COQ5, a ubiquinone biosynthesis methlytransferase, (3) *Bacillus subtilis* spore germination protein C2 (gene: gercB or gerC2), a probable menaquinone biosynthesis methlytransferase, (4) *Lactococcus lactis* gerC2 homolog, (5) *Caenorhabditis elegans* hypothetical protein ZK652.9, and (6) *Leishmania donovani* amastigote-specific protein A41. These are hydrophilic proteins of about 30 Kd (except for ZK652.9 which is 65Kd). They can be picked up in the database by the following patterns.

Consensus pattern: Y-D-x-M-N-x(2)-[LIVM]-S-x(3)-H-x(2)-W (SEQ ID NO:8)
Consensus pattern: R-V-[LIVM]-K-[PV]-G-G-x-[LIVMF]-x(2)-[LIVM]-E-x-S (SEQ ID NO:9)

In Vitro Applications of Polypeptides

Some polypeptides of the invention will have enzymatic activities that are useful in vitro. Enzymes of biosynthetic pathways generally can be used as catalysts for in vitro synthesis of the compounds representing products of the pathway.

III. Methods of Modulating Polypeptide Production

Within the scope of invention are chimeric gene constructs wherein the promoter and the structural coding sequence and/or other regulatory sequences within said constructs are heterologous to each other. By heterologous sequences is meant sequences that are not operatively linked or are contiguous to each other in nature. For example, a promoter from corn is considered heterologous to an *Arabidopsis* coding region sequence. Also, a promoter from a gene encoding a growth factor from corn is considered heterologous to a sequence encoding a receptor from corn. Regulatory element sequences, such as UTRs or 3' end termination sequences that do not originate in nature from the same gene as the coding sequence originates from are considered heterologous to said coding sequence. On the other hand, elements operatively linked in nature are not heterologous. Thus, the promoter and coding portion of a corn gene expressing an amino acid transporter are not heterologous to each other.

Such chimeric polynucleotides are of particular interest when modulating gene expression in a host cell upon transformation of said cell with said chimeric polynucleotide.

Also within the scope of the invention are DNA molecules, whereof at least a part or portion of these DNA molecules is presented in Table 2 of the present invention, and wherein the structural coding sequence is under the control of its own promoter and/or its own regulatory elements. Such DNA molecules are useful for transforming the genome of a host cell or of an organism regenerated from a transformed host cell.

Polynucleotides, whether chimeric or not, are "exogenous to" the genome of an individual host cell or the organism regenerated from said host cell, such as a plant cell or a regenerated plant, when initially or subsequently introduced into said host cell or organism by any means other than by a sexual cross. Examples of means by which this can be accomplished are described below, and include *Agrobacterium*-mediated transformation (of dicots—e.g. Salomon et al. *EMBO J.* 3:141 (1984); Herrera-Estrella et al. *EMBO J.* 2:987 (1983); A. C. Vergunst et al, *Nucleic Acids Res.* 26:11, 2729 (1998); of monocots, representative papers are those by Escudero et al., *Plant J.* 10:355 (1996), Ishida et al., *Nature Biotechnology* 14:745 (1996), May et al., *Bio/Technology* 13:486 (1995)), biolistic methods (Armaleo et al., *Current Genetics* 17:97 1990)), electroporation, in planta techniques, and the like. Such a plant containing the exogenous nucleic acid is referred to here as an R1 generation transgenic plant. Transgenic plants which arise from a sexual cross with another parent line or by selfing are "descendants or the progeny" of a R1 plant and are generally called Fn plants or Sn plants, respectively, n meaning the number of generations.

The SDFs prepared as described herein can be used to prepare expression cassettes useful in a number of techniques for suppressing or enhancing expression.

Modulating Activity:

At least one activity attributed to the domain or related polypeptide of an MLS can be modulated with an antisense, ribozyme, or knockout construct that exhibits at least 70% sequence identity to an MLS of the instant invention.

III.A. Suppression

Expression cassettes of the invention can be used to suppress expression of endogenous genes which comprise the SDF sequence. Inhibiting expression can be useful, for instance, to tailor the ripening characteristics of a fruit (Oeller et al., *Science* 254:437 (1991)) or to influence seed size (WO98/07842) or or to provoke cell ablation (Mariani et al., *Nature* 357: 384-387 (1992).

As described by ways of the examples above, a number of methods can be used to inhibit gene expression in plants, such as antisense, ribozyme, introduction of "exogenous" genes into a host cell, insertion of polynucleotide sequence into the coding sequence and/or the promoter of the endogenous gene of interest, and the like.

III.A.1. Antisense

An expression cassette as described above can be transformed into a host cell or plant to produce an antisense strand of RNA. In plant cells, it has been suggested that antisense RNA inhibits gene expression by preventing the accumulation of mRNA which encodes the enzyme of interest, see, e.g., Sheehy et al., *Proc. Nat. Acad. Sci. USA*, 85:8805 8809 (1988), and Hiatt et al., U.S. Pat. No. 4,801, 340.

III.A.2. Ribozymes

Similarly, ribozyme constructs can be transformed into a plant to cleave mRNA and down-regulate translation.

III.A.3. Co-Suppression

Another method of suppression is by introducing an exogenous copy of the gene to be suppressed. Introduction of expression cassettes in which a nucleic acid is configured in the sense orientation with respect to the promoter has been shown to be an effective means by which to block the transcription of target genes. A detailed description of this method is described above.

III.A.4. Insertion of Sequences into the Gene to be Modulated

Yet another means of suppressing gene expression is to insert a polynucleotide into the gene of interest to disrupt transcription or translation of the gene. Homologous recombination can be used to target a polynucleotide insert to a gene by flanking the polynucleotide insert with sequences that are substantially similar to the gene to be disrupted. The sequence from Table 2, fragments thereof, and substantially similar sequence thereto can be used for homologous recombination.

In addition, random insertion of polynucleotides into a host cell genome can also be used to disrupt the gene of interest (Azpiroz-Leehan et al., *Trends in Genetics* 13:152 (1997)). In this method, screening for clones from a library containing random insertions is preferred for identifying those that have polynucleotides inserted into the gene of interest. Such screening can be performed using probes and/or primers described above based on the sequence from Table 2, fragments thereof, and substantially similar sequence thereto. The screening can also be performed by selecting clones or R1 plants having a desired phenotype.

III.A.5. Promoter Modulation

In activation of the promoter that drives a gene of interest can modulate transcription and translation, and therefore expression. For example, triple helices can be formed using oligonucleotides based on the sequence from Table 2, fragments thereof, and substantially similar sequence thereto. The oligonucleotide can be delivered to the host cell can bind to the promoter in the genome to form a triple helix and prevent transcription. Additionally, a vector capable of producing the oligonucleotide can be inserted into the host cell to deliver the oligonucleotide.

Alternatively, an endogenous suppressor element of a promoter can be duplicated or an exogenous suppressor element can be introduced into the promoter of a gene to be down-regulated.

III.A.6. Expression of Mutants

An alternative method for inhibiting gene function is through the use of dominant negative mutants. These mutants will not exhibit an undesired activity of the native protein. Over-expression of these mutants can titrate out the undesired activity of the native protein. For example, the inactive mutant may bind to the same receptor as the native protein, preventing the native protein from activating a signal transduction pathway. Alternatively, the dominant-negative mutant can be an inactive enzyme still capable of binding to the same substrate as the native protein.

Dominant-negative mutants also can act upon the native protein itself to prevent activity. For example, the native protein may be active only as a homo- or hetero-multimer. Incorporation of an inactive subunit with a native subunit(s) can inhibit activity of the complex.

Thus, gene function can be modulated by insertion of an expression construct encoding a dominant-negative mutant into a host cell of interest.

III.B. Enhanced Expression

Enhanced expression of a gene of interest in a host cell can be accomplished by either (1) insertion of an exogenous gene; or (2) promoter modulation.

III.B.1. Insertion of an Exogenous Gene

Insertion of an expression construct encoding an exogenous gene can boost the number of gene copies for expression in a host cell. Such genes can either encode the native protein that is of interest or can encode a variant that exhibits enhanced activity as compared to the native. Such genes encoding proteins of interest can be constructed from the sequence from Table 2, fragments thereof, and from sequences substantially similar thereto. Such an exogenous gene can include either a constitutive promoter permitting expression in any cell in a host organism or a promoter that directs expression only in particular cells or times during a host cell life cycle or in response to an environmental stimulus.

III.B.2. Promoter Modulation

Some promoters require binding of a regulatory protein to be activated. Other promoters may need a protein that signals a promoter binding protein to expose a polymerase binding site. In either case, over-expression of such proteins can be used to enhance expression of a gene of interest by increasing the activation time of the promoter. Promotor activity can sometimes be increased by duplicating an enhancer element of the promoter or by introducing an exogenous enhancer element.

IV. Vector Construction

To use isolated SDFs of the present invention or a combination of them or parts and/or mutants and/or fusions of said SDFs in the above techniques, recombinant DNA vectors which comprise said SDFs and are suitable for transformation of cells, such as plant cells, are usually prepared.

A DNA sequence coding for the desired polypeptide, for example a cDNA sequence encoding a full length protein, will preferably be combined with transcriptional and translational initiation regulatory sequences which will direct the transcription of the sequence from the gene in the intended tissues of the transformed plant. Typically, a vector will comprise the exogenous gene, which in its turn comprises an SDF of the present invention, to be introduced within the genome of said host cell, and which gene may be an antisense construct, a ribozyme construct, or a structural coding sequence with any desired transcriptional and/or translational regulatory sequences, such as promoters, 3' end termination sequences the vector can further comprise origins of replication, markers, homologous sequences, introns, etc.

IV.A. Coding Sequences and Their Uses

Generally, the sequence comprised in the transformation vector and to be introduced within the genome of the host cell does not need to be absolutely identical with an SDF of the present invention. Also, it is not necessary for it to be full length, relative to either the primary transcription product or fully processed mRNA. Use of a less than full-length sequence may be preferred to avoid concurrent production of some plants that are overexpressors. Furthermore, the introduced sequence need not have the same intron or exon pattern as a native gene. Also, heterologous non-coding segments can be incorporated into the coding sequence that will not change the desired amino acid sequence of the polypeptide to be produced.

IV.B. Promoters

If an SDF is found to encode a protein with desirable characteristics, its over-expression can be controlled so that its accumulation can be manipulated in an organ- or tissue-specific manner utilizing a promoter that has such specificity.

Likewise, if the promoter of an SDF (or an SDF that includes a promoter) is found to be tissue-specific or developmentally regulated, such a promoter can be utilized to drive the expression of a specific gene of interest (e.g., seed storage protein or root-specific protein). Thus, the level of accumulation of a particular protein can be manipulated or its spatial localization in an organ or tissue specific manner can be altered.

As explained above, introducing an exogenous SDF from the same species or an orthologous SDF from another species can modulate the expression of a native gene corresponding to that SDF of interest. Such an SDF construct can be under the control of either a constitutive promoter (e.g., the promoter of the 35S gene of the cauliflower mosaic virus or the promotor of the gene encoding the cowpea trypsin inhibitor) or a highly regulated inducible promoter (e.g., a copper inducible promoter). The promoter of interest can initially either be endogenous or heterologous to the species being transformed. When re-introduced into the genome of said species, such promoter becomes "exogenous" to said species.

For over-expression, a plant promoter fragment may be employed that will direct expression of the gene in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1' or 2' promoter derived from T DNA of Agrobacterium tumefaciens, and other transcription initiation regions from various plant genes known to those of skill.

Alternatively, the plant promoter may direct expression of an SDF of the invention in a specific tissue (tissue specific promoters) or may be otherwise under more precise environmental control (inducible promoters). Examples of tissue specific promoters under developmental control include promoters that initiate transcription only in certain tissues, such as root, ovule, fruit, seeds, or flowers. The promoter from a LEC1 gene, described in copending application U.S. Ser. No. 09/103,478, is particularly useful for directing gene expression so that a desired gene product is located in embryos or seeds. Other suitable promoters include those from genes encoding storage proteins or the lipid body membrane protein, oleosin. A few root-specific promoters are noted above. Examples of environmental conditions that may affect transcription by inducible promoters include anaerobic conditions, elevated temperature, or the presence of light. The promoter-SDF construct can be made using standard recombinant DNA techniques (Sambrook et al. 1989).

IV.C. Other Elements

If proper polypeptide expression is desired, a polyadenylation region at the 3'-end of the coding region should be included. The polyadenylation region can be derived from the natural gene, from a variety of other plant genes, or from T-DNA.

The vector comprising the sequences (e.g., promoters or coding regions) from genes of the invention will typically comprise a marker gene that confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosulfooron or phosphinotricin.

V. Transformation Techniques

The SDF constructs of the invention can be introduced into the species of interest by Agrobacterium-mediated transformation or by other means of transformation (e.g., particle gun bombardment) as referenced below. Over-expression of an SDF transgene can lead to co-suppression of the homologous gene thereby creating some alterations in the phenotypes of the transformed species as demonstrated by similar analysis of the chalcone synthase gene (Napoli et al., Plant Cell 2:279 (1990) and van der Krol et al., Plant Cell 2:291).

A wide range of techniques for inserting exogenous polynucleotides are known for a number of host cells, including, without limitation, bacterial, yeast, mammalian, insect cells.

Techniques for transforming a wide variety of higher plant species are well known and described in the technical and scientific literature. See, e.g. Weising et al., Ann. Rev. Genet. 22:421 477 (1988); and Christou, Euphytica, v. 85, n. 1-3:13-27, (1995).

DNA constructs of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment. Alternatively, the DNA constructs may be combined with suitable T DNA flanking regions and introduced into a conventional Agrobacterium tumefaciens host vector. The virulence functions of the Agrobacterium tumefaciens host will direct the insertion of the construct and adjacent marker into the plant cell DNA when the cell is infected by the bacteria (Vergunst et al., Nucl. Acids. Res. 26:2729 (1998) (site-directed integration using a Cre-Lox recombinase system); McCormac et al., Mol. Biotechnol. 8:199 (1997); Hamilton, Gene 200:107 (1997)); Salomon et al. EMBO J. 3:141 (1984); Herrera-Estrella et al. EMBO J. 2:987(1983).

Microinjection techniques are known in the art and well described in the scientific and patent literature. The introduction of DNA constructs using polyethylene glycol precipitation is described in Paszkowski et al. EMBO J. 3:2717 2722 (1984). Electroporation techniques are described in Fromm et al. Proc. Natl Acad. Sci. USA 82:5824 (1985). Ballistic transformation techniques are described in Klein et al. Nature 327:773 (1987). Agrobacterium tumefaciens mediated transformation techniques, including disarming and use of binary vectors, are well described in the scientific literature. See, for example Hamilton, C M., Gene 200:107 (1997); Müller et al. Mol. Gen. Genet. 207:171 (1987); Komari et al. Plant J. 10:165 (1996); Venkateswarlu et al. Biotechnology 9:1103 (1991) and Gleave, A P., Plant Mol. Biol. 20:1203 (1992); Graves and Goldman, Plant Mol. Biol. 7:34 (1986) and Gould et al., Plant Physiology 95:426 (1991).

Transformed plant cells which are derived by any of the above transformation techniques can be cultured to regenerate a whole plant that possesses the transformed genotype and thus the desired phenotype such as seedlessness. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., Protoplasts Isolation and Culture in "Handbook of Plant Cell Culture," pp. 124 176, MacMillilan Publishing Company, New York, 1983; and Binding, Regeneration of Plants, Plant Protoplasts, pp. 21 73, CRC Press, Boca Raton, 1988. Regeneration can also be obtained from plant callus, explants, organs, or parts thereof. Such regeneration techniques are described generally in Klee et al. Ann. Rev. of Plant Phys. 38:467 486 (1987). Regeneration of monocots (rice) is described by Hosoyama et al. (*Biosci. Biotechnol. Biochem.* 58:1500 (1994)) and by Ghosh et al. (*J. Biotechnol.* 32:1 (1994)). The nucleic acids of the invention can be used to confer desired traits on essentially any plant.

Thus, the invention has use over a broad range of plants, including species from the genera *Asparagus, Atropa, Avena, Brassica, Citrus, Citrullus, Capsicum, Cucumis, Cucurbita, Daucus, Fragaria, Glycine, Gossypium, Helianthus, Heterocallis, Hordeum, Hyoscyamus, Lactuca, Linum, Lolium, Lycopersicon, Malus, Manihot, Majorana, Medicago, Nicotiana, Oryza, Panieum, Pannesetum, Persea, Pisum, Pyrus, Prunus, Raphanus, Secale, Senecio, Sinapis, Solanum, Sorghum, Trigonella, Triticum, V'tis, Vigna,* and *Zea.*

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

VI. Antibodies

Isolated polypeptides can also be utilized to produce antibodies. Polypeptides of the invention can generally be used, for example, as antigens for raising antibodies by known techniques. The resulting antibodies are useful as reagents for determining the distribution of the antigen protein within the tissues of a plant or within a cell of a plant. The antibodies are also useful for examining the expression level of proteins in various tissues, for example in a wild-type plant or following genetic manipulation of a plant, by methods such as Western blotting.

Antibodies of the present invention, both polyclonal and monoclonal, may be prepared by conventional methods. In general, the polypeptides of the invention are first used to immunize a suitable animal, such as a mouse, rat, rabbit, or goat. Rabbits and goats are preferred for the preparation of polyclonal sera due to the volume of serum obtainable, and the availability of labeled anti-rabbit and anti-goat antibodies. Immunization is generally performed by mixing or emulsifying the protein in saline, preferably in an adjuvant such as Freund's complete adjuvant, and injecting the mixture or emulsion parenterally (generally subcutaneously or intramuscularly). A dose of 50-200 µg/injection is typically sufficient. Immunization is generally boosted 2-6 weeks later with one or more injections of the protein in saline, preferably using Freund's incomplete adjuvant. One may alternatively genereate antibodies by in vitro immunization using methods known in the art, which for the purposes of this invention is considered equivalent to in vivo immunization.

Polyclonal antiserum is obtained by bleeding the immunized animal into a glass or plastic container, incubating the blood at 25° C. for one hour, followed by incubating the blood at 4° C. for 2-18 hours. The serum is recovered by centrifugation (e.g., 1,000×g for 10 minutes). About 20-50 ml per bleed may be obtained from rabbits.

Monoclonal antibodies (MAb) are prepared using the method of Kohler and Milstein, *Nature* 256: 495, (1975) or modification thereof. Typically, a mouse or rat is immunized as described above. However, rather than bleeding the animal to extract serum, the spleen (and optionally several large lymph nodes) is removed and dissociated into single cells. If desired, the spleen cells may be screened (after removal of nonspecifically adherent cells) by applying a cell suspension to a plate or well coated with the protein antigen. B-cells expressing membrane-bound immunoglobulin specific for the antigen bind to the plate, and are not rinsed away with the rest of the suspension. Resulting B-cells, or dissociated spleen cells, are then induced to fuse with myeloma cells to form hybridomas, and are cultured in a selective medium (e.g., hypoxanthine, aminopterin, thymidine medium, "HAT"). The resulting hybridomas are plated by limiting dilution, and are assayed for the production of antibodies which bind specifically to the immunizing antigen (and which do not bind to unrelated antigens). The selected Mab-secreting hybridomas are then cultured either in vitro (e.g., in tissue culture bottles or hollow fiber reactors), or in vivo (as ascites in mice).

If desired, the antibodies (whether polyclonal or monoclonal) may be labeled using conventional techniques. Suitable labels include fluorophores, chromophores, radioactive atoms (particularly $^{32}P$ and $^{125}I$), electron-dense reagents, enzymes, and ligands having specific binding partners. Enzymes are typically detected by their activity. For example, horseradish peroxidase is usually detected by its ability to convert 3,3',5,5'-tetramethylbenzidine (TNB) to a blue pigment, quantifiable with a spectrophotometer. "Specific binding partner" refers to a protein capable of biding a ligand molecule with high specificity, as for example in the case of an antigen and a monoclonal antibody specific therefor. Other specific binding partners include biotin and avidin or streptavidin, IgG and protein A, and the numerous receptor-ligand couples known in the art. It should be understood that the above description is not mean to categorize the various labels into distinct modes. For example, $^{125}I$ may serve as a radioactive label or as an electron-dense reagent. HRP may serve as an enzyme or as an antigen for a Mab. Further one may combine various labels for desired effect. For example, Mabs and avidin also require labels in the practice of this invention: thus, one might label a Mab with biotin, and detect its presence with avidin labeled with $^{125}I$, or with an anti-biotin Mab labeled with HRP. Other permutations and possibilities will be readily apparent to those of ordinary skill in the art, and are considered as equivalents within the scope of the instant invention.

Exemplary sequences of SDFs identified are provided in Table 2.

The invention being thus described, it will be apparent to one of ordinary skill in the art that various modifications of the materials and methods for practicing the invention can be made. Such modifications are to be considered within the scope of the invention as defined by the following claims.

Each of the references from the patent and periodical literature cited herein are hereby expressly incorporated in their entirety by such citation.

SEQUENCE LISTING

<160> NUMBER OF SEQ ID NOS: 9

<210> SEQ ID NO 1
<211> LENGTH: 1169
<212> TYPE: DNA

<213> ORGANISM: Arabidopsis thaliana

<400> SEQUENCE: 1

```
tcgtttgtgt ttttgattgg cggagaattg gtgatagata agcttcttct tccctcttct    60
caacttggtg gatctgtcat cgatggcctc tttgatgctc aacggggcca ttaccttccc   120
caaaggttta ggttcccctg gttccaattt gcatgccaga tcgattcctc ggccgacctt   180
actctcagtt acccgaacct ccacacctag actctcggtg gctactagat gcagcagcag   240
cagcgtgtcg tcttcccggc catcggcgca acctaggttc attcagcaca agaaggaggc   300
ttactggttc tacaggttct tatccatcgt atacgaccat gtcatcaatc ctgggcattg   360
gaccgaggat atgagagacg acgctcttga gccagcggat ctcagccatc cggacatgcg   420
agtggtcgat gtcggcggcg gaactggttt cactactctg gcatagtca agacagtgaa   480
ggccaagaat gtgaccattc tggaccagtc gccacatcag ctggccaaag caaagcaaaa   540
ggagccgttg aaagaatgca agatcgtcga gggagatgct gaggatcttc ctttccaac   600
cgattatgct gacagatacg tttctgctgg aagcattgag tactggccgg accgcagag   660
gggaataagg gaagcgtaca gggttctcaa gatcggtggc aaagcgtgtc tcatcggccc   720
tgtctaccca accttctggc tctctcgctt cttttctgat gtctggatgc tcttccccaa   780
ggaggaagaa tacattgagt ggttcaagaa tgccggtttc aaggacgttc agctcaagag   840
gattggcccc aagtggtacc gtggtgttcg caggcacggc cttatcatgg atattctgt    900
cactggtgtt aaacctgcct ccggtgactc tcctctccag cttggtccaa aggaagagga   960
cgtagagaag cctgtcaaca ccccttctc cttcttggga cgcttcctcc tgggaactct  1020
agcagctgcc tggtttgtgt taatccctat ctacatgtgg atcaaggatc agatcgttcc  1080
caaagaccaa cccatctgat ccttctcttc taggacatga tcattgtatc attgtaaacc  1140
cctcttgtgg taaagaaaga ttcgagtcc                                    1169
```

<210> SEQ ID NO 2
<211> LENGTH: 339
<212> TYPE: PRT
<213> ORGANISM: Arabidopsis thaliana
<220> FEATURE:
<221> NAME/KEY: VARIANT
<222> LOCATION: 339
<223> OTHER INFORMATION: Xaa = Any Amino Acid

<400> SEQUENCE: 2

```
Met Ala Ser Leu Met Leu Asn Gly Ala Ile Thr Phe Pro Lys Gly Leu
  1               5                  10                  15

Gly Ser Pro Gly Ser Asn Leu His Ala Arg Ser Ile Pro Arg Pro Thr
                 20                  25                  30

Leu Leu Ser Val Thr Arg Thr Ser Thr Pro Arg Leu Ser Val Ala Thr
             35                  40                  45

Arg Cys Ser Ser Ser Val Ser Ser Arg Pro Ser Ala Gln Pro
 50                  55                  60

Arg Phe Ile Gln His Lys Lys Glu Ala Tyr Trp Phe Tyr Arg Phe Leu
 65                  70                  75                  80

Ser Ile Val Tyr Asp His Val Ile Asn Pro Gly His Trp Thr Glu Asp
                 85                  90                  95

Met Arg Asp Asp Ala Leu Glu Pro Ala Asp Leu Ser His Pro Asp Met
                100                 105                 110

Arg Val Val Asp Val Gly Gly Gly Thr Gly Phe Thr Thr Leu Gly Ile
            115                 120                 125
```

```
Val Lys Thr Val Lys Ala Lys Asn Val Thr Ile Leu Asp Gln Ser Pro
    130                 135                 140

His Gln Leu Ala Lys Ala Lys Gln Lys Glu Pro Leu Lys Glu Cys Lys
145                 150                 155                 160

Ile Val Glu Gly Asp Ala Glu Asp Leu Pro Phe Pro Thr Asp Tyr Ala
                165                 170                 175

Asp Arg Tyr Val Ser Ala Gly Ser Ile Glu Tyr Trp Pro Asp Pro Gln
            180                 185                 190

Arg Gly Ile Arg Glu Ala Tyr Arg Val Leu Lys Ile Gly Lys Ala
        195                 200                 205

Cys Leu Ile Gly Pro Val Tyr Pro Thr Phe Trp Leu Ser Arg Phe Phe
    210                 215                 220

Ser Asp Val Trp Met Leu Phe Pro Lys Glu Glu Tyr Ile Glu Trp
225                 230                 235                 240

Phe Lys Asn Ala Gly Phe Lys Asp Val Gln Leu Lys Arg Ile Gly Pro
                245                 250                 255

Lys Trp Tyr Arg Gly Val Arg Arg His Gly Leu Ile Met Gly Tyr Ser
            260                 265                 270

Val Thr Gly Val Lys Pro Ala Ser Gly Asp Ser Pro Leu Gln Leu Gly
        275                 280                 285

Pro Lys Glu Glu Asp Val Glu Lys Pro Val Asn Asn Pro Phe Ser Phe
    290                 295                 300

Leu Gly Arg Phe Leu Leu Gly Thr Leu Ala Ala Ala Trp Phe Val Leu
305                 310                 315                 320

Ile Pro Ile Tyr Met Trp Ile Lys Asp Gln Ile Val Pro Lys Asp Gln
                325                 330                 335

Pro Ile Xaa

<210> SEQ ID NO 3
<211> LENGTH: 335
<212> TYPE: PRT
<213> ORGANISM: Arabidopsis thaliana
<220> FEATURE:
<221> NAME/KEY: VARIANT
<222> LOCATION: 335
<223> OTHER INFORMATION: Xaa = Any Amino Acid

<400> SEQUENCE: 3

Met Leu Asn Gly Ala Ile Thr Phe Pro Lys Gly Leu Gly Ser Pro Gly
1               5                   10                  15

Ser Asn Leu His Ala Arg Ser Ile Pro Arg Pro Thr Leu Leu Ser Val
            20                  25                  30

Thr Arg Thr Ser Thr Pro Arg Leu Ser Val Ala Thr Arg Cys Ser Ser
        35                  40                  45

Ser Ser Val Ser Ser Ser Arg Pro Ser Ala Gln Pro Arg Phe Ile Gln
    50                  55                  60

His Lys Lys Glu Ala Tyr Trp Phe Tyr Arg Phe Leu Ser Ile Val Tyr
65                  70                  75                  80

Asp His Val Ile Asn Pro Gly His Trp Thr Glu Asp Met Arg Asp Asp
                85                  90                  95

Ala Leu Glu Pro Ala Asp Leu Ser His Pro Asp Met Arg Val Val Asp
            100                 105                 110

Val Gly Gly Gly Thr Gly Phe Thr Thr Leu Gly Ile Val Lys Thr Val
        115                 120                 125

Lys Ala Lys Asn Val Thr Ile Leu Asp Gln Ser Pro His Gln Leu Ala
```

-continued

```
                130                 135                 140
Lys Ala Lys Gln Lys Glu Pro Leu Lys Glu Cys Lys Ile Val Glu Gly
145                 150                 155                 160

Asp Ala Glu Asp Leu Pro Phe Pro Thr Asp Tyr Ala Asp Arg Tyr Val
                165                 170                 175

Ser Ala Gly Ser Ile Glu Tyr Trp Pro Asp Pro Gln Arg Gly Ile Arg
                180                 185                 190

Glu Ala Tyr Arg Val Leu Lys Ile Gly Gly Lys Ala Cys Leu Ile Gly
                195                 200                 205

Pro Val Tyr Pro Thr Phe Trp Leu Ser Arg Phe Ser Asp Val Trp
210                 215                 220

Met Leu Phe Pro Lys Glu Glu Tyr Ile Glu Trp Phe Lys Asn Ala
225                 230                 235                 240

Gly Phe Lys Asp Val Gln Leu Lys Arg Ile Gly Pro Lys Trp Tyr Arg
                245                 250                 255

Gly Val Arg His Gly Leu Ile Met Gly Tyr Ser Val Thr Gly Val
                260                 265                 270

Lys Pro Ala Ser Gly Asp Ser Pro Leu Gln Leu Gly Pro Lys Glu Glu
                275                 280                 285

Asp Val Glu Lys Pro Val Asn Asn Pro Phe Ser Phe Leu Gly Arg Phe
290                 295                 300

Leu Leu Gly Thr Leu Ala Ala Trp Phe Val Leu Ile Pro Ile Tyr
305                 310                 315                 320

Met Trp Ile Lys Asp Gln Ile Val Pro Lys Asp Gln Pro Ile Xaa
                325                 330                 335
```

<210> SEQ ID NO 4
<211> LENGTH: 243
<212> TYPE: PRT
<213> ORGANISM: Arabidopsis thaliana
<220> FEATURE:
<221> NAME/KEY: VARIANT
<222> LOCATION: 243
<223> OTHER INFORMATION: Xaa = Any Amino Acid

<400> SEQUENCE: 4

```
Met Arg Asp Asp Ala Leu Glu Pro Ala Asp Leu Ser His Pro Asp Met
1               5                   10                  15

Arg Val Val Asp Val Gly Gly Thr Gly Phe Thr Thr Leu Gly Ile
                20                  25                  30

Val Lys Thr Val Lys Ala Lys Asn Val Thr Ile Leu Asp Gln Ser Pro
                35                  40                  45

His Gln Leu Ala Lys Ala Lys Gln Lys Glu Pro Leu Lys Glu Cys Lys
    50                  55                  60

Ile Val Glu Gly Asp Ala Glu Asp Leu Pro Phe Pro Thr Asp Tyr Ala
65              70                  75                  80

Asp Arg Tyr Val Ser Ala Gly Ser Ile Glu Tyr Trp Pro Asp Pro Gln
                85                  90                  95

Arg Gly Ile Arg Glu Ala Tyr Arg Val Leu Lys Ile Gly Gly Lys Ala
                100                 105                 110

Cys Leu Ile Gly Pro Val Tyr Pro Thr Phe Trp Leu Ser Arg Phe Phe
                115                 120                 125

Ser Asp Val Trp Met Leu Phe Pro Lys Glu Glu Tyr Ile Glu Trp
            130                 135                 140

Phe Lys Asn Ala Gly Phe Lys Asp Val Gln Leu Lys Arg Ile Gly Pro
145                 150                 155                 160
```

```
Lys Trp Tyr Arg Gly Val Arg Arg His Gly Leu Ile Met Gly Tyr Ser
            165                 170                 175

Val Thr Gly Val Lys Pro Ala Ser Gly Asp Ser Pro Leu Gln Leu Gly
            180                 185                 190

Pro Lys Glu Glu Asp Val Glu Lys Pro Val Asn Asn Pro Phe Ser Phe
            195                 200                 205

Leu Gly Arg Phe Leu Leu Gly Thr Leu Ala Ala Ala Trp Phe Val Leu
            210                 215                 220

Ile Pro Ile Tyr Met Trp Ile Lys Asp Gln Ile Val Pro Lys Asp Gln
225                 230                 235                 240

Pro Ile Xaa

<210> SEQ ID NO 5
<211> LENGTH: 338
<212> TYPE: PRT
<213> ORGANISM: Arabidopsis thaliana

<400> SEQUENCE: 5

Met Ala Ser Leu Met Leu Asn Gly Ala Ile Thr Phe Pro Lys Gly Leu
1               5                   10                  15

Gly Ser Pro Gly Ser Asn Leu His Ala Arg Ser Ile Pro Arg Pro Thr
            20                  25                  30

Leu Leu Ser Val Thr Arg Thr Ser Thr Pro Arg Leu Ser Val Ala Thr
            35                  40                  45

Arg Cys Ser Ser Ser Val Ser Ser Ser Arg Pro Ser Ala Gln Pro
50                  55                  60

Arg Phe Ile Gln His Lys Lys Glu Ala Tyr Trp Phe Tyr Arg Phe Leu
65                  70                  75                  80

Ser Ile Val Tyr Asp His Val Ile Asn Pro Gly His Trp Thr Glu Asp
            85                  90                  95

Met Arg Asp Asp Ala Leu Glu Pro Ala Asp Leu Ser His Pro Asp Met
            100                 105                 110

Arg Val Val Asp Val Gly Gly Gly Thr Gly Phe Thr Thr Leu Gly Ile
            115                 120                 125

Val Lys Thr Val Lys Ala Lys Asn Val Thr Ile Leu Asp Gln Ser Pro
130                 135                 140

His Gln Leu Ala Lys Ala Lys Gln Lys Glu Pro Leu Lys Glu Cys Lys
145                 150                 155                 160

Ile Val Glu Gly Asp Ala Glu Asp Leu Pro Phe Pro Thr Asp Tyr Ala
            165                 170                 175

Asp Arg Tyr Val Ser Ala Gly Ser Ile Glu Tyr Trp Pro Asp Pro Gln
            180                 185                 190

Arg Gly Ile Arg Glu Ala Tyr Arg Val Leu Lys Ile Gly Gly Lys Ala
            195                 200                 205

Cys Leu Ile Gly Pro Val Tyr Pro Thr Phe Trp Leu Ser Arg Phe Phe
            210                 215                 220

Ser Asp Val Trp Met Leu Phe Pro Lys Glu Glu Glu Tyr Ile Glu Trp
225                 230                 235                 240

Phe Lys Asn Ala Gly Phe Lys Asp Val Gln Leu Lys Arg Ile Gly Pro
            245                 250                 255

Lys Trp Tyr Arg Gly Val Arg Arg His Gly Leu Ile Met Gly Tyr Ser
            260                 265                 270

Val Thr Gly Val Lys Pro Ala Ser Gly Asp Ser Pro Leu Gln Leu Gly
            275                 280                 285
```

```
Pro Lys Glu Glu Asp Val Glu Lys Pro Val Asn Asn Pro Phe Ser Phe
    290                 295                 300

Leu Gly Arg Phe Leu Leu Gly Thr Leu Ala Ala Ala Trp Phe Val Leu
305                 310                 315                 320

Ile Pro Ile Tyr Met Trp Ile Lys Asp Gln Ile Val Pro Lys Asp Gln
                325                 330                 335

Pro Ile

<210> SEQ ID NO 6
<211> LENGTH: 255
<212> TYPE: PRT
<213> ORGANISM: Consensus sequence

<400> SEQUENCE: 6

Met Ala Met Leu Asn Gly Pro Leu Gly Ser Pro Arg Leu Arg Leu Thr
1               5                   10                  15

Cys Ser Ser Arg Pro Gln Pro Arg Phe Ile Gln Lys Glu Ala Trp Phe
                20                  25                  30

Tyr Arg Phe Leu Ser Ile Val Tyr Asp Ile Asn Pro Gly His Trp Thr
            35                  40                  45

Glu Asp Met Arg Asp Ala Leu Glu Pro Ala Asp Leu Met Val Val Asp
        50                  55                  60

Val Gly Gly Gly Thr Gly Phe Thr Thr Leu Gly Ile Lys Val Lys Asn
65                  70                  75                  80

Val Thr Ile Leu Asp Gln Ser Pro His Gln Leu Ala Lys Ala Lys Lys
                85                  90                  95

Pro Leu Lys Glu Cys Ile Glu Gly Asp Ala Glu Asp Leu Pro Phe Pro
                100                 105                 110

Thr Asp Tyr Ala Asp Arg Tyr Val Ser Ala Gly Ser Ile Glu Tyr Trp
            115                 120                 125

Pro Asp Pro Gln Arg Gly Ile Arg Glu Ala Tyr Arg Val Leu Lys Gly
        130                 135                 140

Gly Lys Ala Cys Leu Ile Gly Pro Val Tyr Pro Thr Phe Trp Leu Ser
145                 150                 155                 160

Arg Phe Phe Asp Val Trp Met Leu Phe Pro Lys Glu Glu Tyr Ile
                165                 170                 175

Glu Trp Phe Ala Gly Phe Lys Asp Val Gln Leu Lys Arg Ile Gly Pro
            180                 185                 190

Lys Trp Tyr Arg Gly Val Arg Arg His Gly Leu Ile Met Gly Ser Val
        195                 200                 205

Thr Gly Val Lys Pro Ala Ser Gly Asp Ser Pro Leu Gln Leu Gly Pro
    210                 215                 220

Lys Glu Asp Val Lys Pro Val Pro Phe Leu Arg Phe Leu Gly Leu
225                 230                 235                 240

Ala Val Leu Pro Ile Tyr Met Trp Ile Lys Asp Ile Pro Lys Pro
                245                 250                 255

<210> SEQ ID NO 7
<211> LENGTH: 344
<212> TYPE: PRT
<213> ORGANISM: Spinacia oleracea

<400> SEQUENCE: 7

Met Ala Cys Ser Met Leu Asn Gly Val Asp Lys Leu Ala Leu Ile Ser
1               5                   10                  15
```

```
Gly Lys Thr Pro Asn Arg Leu Arg Phe Ser Gly Ser Asp Phe Thr Gly
         20                  25                  30

Ser Tyr Lys Leu Pro Arg Leu Asn Leu Pro Pro Asn Ser Arg Asn Leu
         35                  40                  45

Arg Ala Lys Thr Leu Thr Thr Val Thr Lys Cys Thr Leu Ser Ala Ser
 50                  55                  60

Glu Arg Pro Ala Ser Gln Pro Arg Phe Ile Gln Asn Lys Gln Glu Ala
 65                  70                  75                  80

Phe Trp Phe Tyr Arg Phe Leu Ser Ile Val Tyr Asp Asn Ile Ile Asn
                 85                  90                  95

Pro Gly His Trp Thr Glu Asp Met Arg Asp Val Ala Leu Glu Pro Ala
             100                 105                 110

Asp Leu Asn Asn Arg Asn Met Leu Val Val Asp Val Gly Gly Thr
             115                 120                 125

Gly Phe Thr Thr Leu Gly Ile Ile Lys His Val Asp Pro Lys Asn Val
    130                 135                 140

Thr Ile Leu Asp Gln Ser Pro His Gln Leu Ala Lys Ala Lys Ala Lys
145                 150                 155                 160

Lys Pro Leu Lys Glu Cys Arg Ile Ile Glu Gly Asp Ala Glu Asp Leu
                165                 170                 175

Pro Phe Pro Thr Asp Tyr Ala Asp Arg Tyr Val Ser Ala Gly Ser Ile
            180                 185                 190

Glu Tyr Trp Pro Asp Pro Gln Arg Gly Ile Arg Glu Ala Tyr Arg Val
        195                 200                 205

Leu Lys Leu Gly Gly Lys Ala Cys Leu Ile Gly Pro Val Tyr Pro Thr
    210                 215                 220

Phe Trp Leu Ser Arg Phe Phe Ala Asp Val Trp Met Leu Phe Pro Lys
225                 230                 235                 240

Glu Glu Glu Tyr Ile Glu Trp Phe Gln Lys Ala Gly Phe Lys Asp Val
                245                 250                 255

Gln Leu Lys Arg Ile Gly Pro Lys Trp Tyr Arg Gly Val Arg Arg His
            260                 265                 270

Gly Leu Ile Met Gly Cys Ser Val Thr Gly Val Lys Pro Ala Ser Gly
        275                 280                 285

Asp Ser Pro Leu Gln Leu Gly Pro Lys Val Glu Asp Val Gln Lys Pro
    290                 295                 300

Val His Pro Leu Val Phe Leu Tyr Arg Phe Leu Leu Gly Ala Leu Ala
305                 310                 315                 320

Ser Thr Tyr Tyr Val Leu Val Pro Ile Tyr Met Trp Ile Lys Asp Lys
                325                 330                 335

Ile Phe Pro Lys Gly Met Pro Leu
            340

<210> SEQ ID NO 8
<211> LENGTH: 16
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: 3
<223> OTHER INFORMATION: Xaa= Any Amino Acid
<220> FEATURE:
<221> NAME/KEY: VARIANT
<222> LOCATION: 6, 7
<223> OTHER INFORMATION: Xaa= Any Amino Acid
<220> FEATURE:
```

```
<221> NAME/KEY: VARIANT
<222> LOCATION: 8
<223> OTHER INFORMATION: Xaa= Leu, Ile, Val, or Met
<220> FEATURE:
<221> NAME/KEY: VARIANT
<222> LOCATION: 10, 11, 12
<223> OTHER INFORMATION: Xaa= Any Amino Acid
<220> FEATURE:
<221> NAME/KEY: VARIANT
<222> LOCATION: 14, 15
<223> OTHER INFORMATION: Xaa= Any Amino Acid

<400> SEQUENCE: 8

Tyr Asp Xaa Met Asn Xaa Xaa Xaa Ser Xaa Xaa Xaa His Xaa Xaa Trp
 1               5                  10                  15

<210> SEQ ID NO 9
<211> LENGTH: 15
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: 3
<223> OTHER INFORMATION: Xaa= Leu, Ile, Val, or Met
<220> FEATURE:
<221> NAME/KEY: VARIANT
<222> LOCATION: 5
<223> OTHER INFORMATION: Xaa= Pro or Val
<220> FEATURE:
<221> NAME/KEY: VARIANT
<222> LOCATION: 8
<223> OTHER INFORMATION: Xaa= Any Amino Acid
<220> FEATURE:
<221> NAME/KEY: VARIANT
<222> LOCATION: 9
<223> OTHER INFORMATION: Xaa= Lue, Ile, Val, Met or Phe
<220> FEATURE:
<221> NAME/KEY: VARIANT
<222> LOCATION: 10, 11
<223> OTHER INFORMATION: Xaa= Any Amino cid
<220> FEATURE:
<221> NAME/KEY: VARIANT
<222> LOCATION: 12
<223> OTHER INFORMATION: Xaa= Leu, Ile, Val, or Met
<220> FEATURE:
<221> NAME/KEY: VARIANT
<222> LOCATION: 14
<223> OTHER INFORMATION: Xaa= Any Amino Acid

<400> SEQUENCE: 9

Arg Val Xaa Lys Xaa Gly Gly Xaa Xaa Xaa Xaa Xaa Glu Xaa Ser
 1               5                  10                  15
```

What is claimed is:

1. An isolated polynucleotide having a nucleic acid sequence that encodes a polypeptide having methyltransferase activity, wherein said polypeptide comprises an amino acid sequence with at least 95 percent identity to the sequence set forth in SEQ ID NO:2.

* * * * *